United States Patent
Henderkott et al.

(10) Patent No.: US 9,341,586 B2
(45) Date of Patent: May 17, 2016

(54) THERMOGRAPHIC INSPECTION TECHNIQUES

(71) Applicant: Rolls-Royce Corporation, Indianapolis, IN (US)

(72) Inventors: Joseph Peter Henderkott, Westfield, IN (US); Kong Ma, Carmel, IN (US)

(73) Assignee: Rolls-Royce Corporation, Indianapolis, IN (US)

( * ) Notice: Subject to any disclaimer, the term of this patent is extended or adjusted under 35 U.S.C. 154(b) by 0 days.

(21) Appl. No.: 14/559,601

(22) Filed: Dec. 3, 2014

(65) Prior Publication Data

US 2015/0161778 A1 Jun. 11, 2015

Related U.S. Application Data

(60) Provisional application No. 61/912,946, filed on Dec. 6, 2013.

(51) Int. Cl.
*G06K 9/00* (2006.01)
*G01N 25/72* (2006.01)
(Continued)

(52) U.S. Cl.
CPC *G01N 25/72* (2013.01); *F01D 5/00* (2013.01); *F01D 5/14* (2013.01); *F01D 5/147* (2013.01); *F01D 5/186* (2013.01); *F01D 5/187* (2013.01); *F01D 9/041* (2013.01); *F01D 17/02* (2013.01); *F01D 17/10* (2013.01); *F01D 17/12* (2013.01); *F01D 17/14* (2013.01); *F01D 17/20* (2013.01); *F01D 17/24* (2013.01); *F01D 21/10* (2013.01); *F01D 25/002* (2013.01); *G01F 1/00* (2013.01);
(Continued)

(58) Field of Classification Search
CPC .................. G06T 7/001; G06T 7/0008; G06T 2207/10048; G06T 7/0026; G06T 2207/30164; H04N 5/33
USPC .......................................................... 348/129
See application file for complete search history.

(56) References Cited

U.S. PATENT DOCUMENTS 4,338,520 A 7/1982 Stewart
5,464,479 A 11/1995 Kenton et al.
(Continued)

FOREIGN PATENT DOCUMENTS

CA 2229630 A1 9/1998
EP 2189941 A2 5/2010
(Continued)

OTHER PUBLICATIONS

U.S. Appl. No. 61/912,946, by Joseph Peter Henderkott et al., filed Dec. 6, 2013.
(Continued)

*Primary Examiner* — Ruiping Li
(74) *Attorney, Agent, or Firm* — Shumaker & Sieffert, P.A.

(57) ABSTRACT

A system may include a source of dry ice, a thermal camera, and a computing device. The computing device may be configured to control the source of dry ice to cause dry ice to be introduced into an internal passage of a tested component. The tested component may include debris within the internal passage, and the dry ice may remove at least some of the debris from the internal passage. The computing device also may be configured to receive, from the thermal camera, thermographic image data representative of the thermal response of the tested component and output a representation based on the thermographic image data.

14 Claims, 11 Drawing Sheets

(51) Int. Cl.

| | | |
|---|---|---|
| G06T 7/00 | (2006.01) | |
| G01F 1/00 | (2006.01) | |
| G01J 5/50 | (2006.01) | |
| G01K 13/02 | (2006.01) | |
| G06T 3/00 | (2006.01) | |
| H04N 5/33 | (2006.01) | |
| F01D 5/14 | (2006.01) | |
| F01D 5/18 | (2006.01) | |
| F01D 17/02 | (2006.01) | |
| F01D 17/10 | (2006.01) | |
| F01D 17/12 | (2006.01) | |
| F01D 17/14 | (2006.01) | |
| F01D 17/20 | (2006.01) | |
| F01D 17/24 | (2006.01) | |
| F01D 21/10 | (2006.01) | |
| F01D 25/00 | (2006.01) | |
| F01D 5/00 | (2006.01) | |
| F01D 9/04 | (2006.01) | |
| G01J 5/00 | (2006.01) | |

(52) U.S. Cl.
CPC ............... *G01J 5/505* (2013.01); *G01K 13/02* (2013.01); *G06T 3/0068* (2013.01); *G06T 7/001* (2013.01); *G06T 7/0008* (2013.01); *G06T 7/0026* (2013.01); *G06T 7/0032* (2013.01); *H04N 5/33* (2013.01); *F05D 2260/83* (2013.01); *G01J 2005/0081* (2013.01); *G06T 2207/10048* (2013.01); *G06T 2207/20076* (2013.01); *G06T 2207/30164* (2013.01)

(56) References Cited

U.S. PATENT DOCUMENTS

| | | | |
|---|---|---|---|
| 6,173,068 B1 | 1/2001 | Prokoski | |
| 6,426,152 B1 | 7/2002 | Johnson et al. | |
| 6,537,619 B2 | 3/2003 | Johnson et al. | |
| 6,732,582 B2 | 5/2004 | Bunker et al. | |
| 6,751,340 B2 | 6/2004 | Prokoski | |
| 6,909,800 B2 | 6/2005 | Vaidyanathan | |
| 7,119,338 B2 | 10/2006 | Thompson et al. | |
| 7,287,902 B2 | 10/2007 | Safai et al. | |
| 7,365,330 B1 | 4/2008 | Sun | |
| 7,388,980 B2 | 6/2008 | Vaidyanathan | |
| 7,509,735 B2 | 3/2009 | Philip et al. | |
| 7,513,964 B2 | 4/2009 | Ritter et al. | |
| 7,605,924 B2 | 10/2009 | Howard et al. | |
| 7,661,877 B2 | 2/2010 | Kitahara | |
| 7,689,003 B2 | 3/2010 | Shannon et al. | |
| 7,805,251 B2 | 9/2010 | Ringermacher et al. | |
| 7,822,268 B2 | 10/2010 | Rothenfusser et al. | |
| 7,909,507 B2 | 3/2011 | Bunker et al. | |
| 7,966,883 B2 | 6/2011 | Lorraine et al. | |
| 8,010,315 B2 | 8/2011 | Wu et al. | |
| 8,055,054 B2 | 11/2011 | Ringermacher et al. | |
| 8,167,482 B2 | 5/2012 | Hatcher | |
| 8,197,129 B2 | 6/2012 | Goldammer et al. | |
| 8,203,606 B2 | 6/2012 | Avila et al. | |
| 8,221,825 B2 | 7/2012 | Reitz et al. | |
| 8,238,642 B2 | 8/2012 | Wu et al. | |
| 8,244,025 B2 | 8/2012 | Davis et al. | |
| 8,287,183 B2 | 10/2012 | Shepard et al. | |
| 8,442,301 B2 | 5/2013 | Dragovich et al. | |
| 2006/0191622 A1 | 8/2006 | Ritter et al. | |
| 2007/0238954 A1 | 10/2007 | White et al. | |
| 2008/0101683 A1 | 5/2008 | Zombo et al. | |
| 2009/0031564 A1 | 2/2009 | Meier | |
| 2009/0297336 A1 | 12/2009 | Allen et al. | |
| 2010/0191541 A1 | 7/2010 | Prokoski | |
| 2011/0125423 A1 | 5/2011 | Allen et al. | |
| 2011/0149015 A1 | 6/2011 | Lin | |
| 2011/0235672 A1* | 9/2011 | Shepard | F01D 5/186 374/45 |
| 2011/0293166 A1 | 12/2011 | Sinbar et al. | |
| 2012/0211548 A1 | 8/2012 | Clark et al. | |
| 2012/0274778 A1 | 11/2012 | Knight et al. | |
| 2013/0026365 A1 | 1/2013 | Jahnke et al. | |
| 2013/0041614 A1 | 2/2013 | Shepard et al. | |
| 2013/0160609 A1 | 6/2013 | Kool et al. | |
| 2013/0163849 A1 | 6/2013 | Jahnke et al. | |
| 2013/0199040 A1 | 8/2013 | Dudeck et al. | |
| 2014/0063228 A1* | 3/2014 | Boles | G02B 23/24 348/82 |

FOREIGN PATENT DOCUMENTS

| | | |
|---|---|---|
| EP | 2428795 A1 | 3/2012 |
| JP | 2006189410 A | 7/2006 |
| WO | 03038238 A2 | 5/2003 |
| WO | 2004048775 A2 | 6/2004 |
| WO | 2001131263 A1 | 10/2011 |

OTHER PUBLICATIONS

Nirmalan et al., "The Measurement of Full-Surface Internal Heat Transfer Coefficients for Turbine Airfoils Using a Nondestructive Thermal Inertia Technique," Transactions of the ASME: Journal of Turbomachinery, American Society of Mechanical Engineers, vol. 125, Jan. 2003, 7 pp.

Extended Search Report from counterpart European Application No. 14196392.6, dated Apr. 8, 2015, 7 pp.

Cui, et al., "Visualisierung von Infrarotbildern auf geometrisch komplizierten Pruefobjekten," Thermographie Kolloquium, Jan. 2009, 8 pp.

Oswald-Tranta, et al., "Fusion of geometric and thermographic data for automated defect detection," Journal of Electronic Imaging, vol. 21, No. 2, Apr. 2012, 9 pp.

Office Action from U.S. Appl. No. 141559,288, dated Nov. 13, 2015, 16 pp.

Office Action from U.S. Appl. No. 141559,347, dated Nov. 13, 2015, 18 pp.

Response to the Office Action mailed Nov. 13, 2015, from U.S. Appl. No. 14/559,347, filed Dec. 11, 2015, 11 pp.

Response to the Office Action mailed Nov. 13, 2015, from U.S. Appl. No. 14/559,288, filed Dec. 11, 2015, 13 pp.

Office Action from U.S. Appl. No. 14/559,347, dated Jan. 15, 2016, 16 pp.

Response to European Office Action dated Jun. 15, 2016, from counterpart European application No. 14196392.6, filed Dec. 2, 2015, 11 pp.

Notice of Allowance from U.S. Appl. No. 14/559,288, mailed Dec. 3, 2014, 9 pp.

* cited by examiner

THERMOGRAPHIC INSPECTION TECHNIQUES

This application claims the benefit of U.S. Provisional Application No. 61/912,946, filed Dec. 6, 2013, which is incorporated herein by reference in its entirety.

TECHNICAL FIELD

The disclosure relates to thermographic inspection.

BACKGROUND

Nondestructive testing of components may be used to identify anomalies, defects, or damaged portions of components without further damaging the component. One type of nondestructive testing is thermography. In thermography, a thermal camera is used to capture image data representative of a surface temperature of a component in response to an applied heat or cooling source. In flash thermography, a heat source, such as a flash lamp, is used to apply heat to the outer surface of the component. The thermal camera captures image data representative of the surface temperature of the component over time, which provides the thermal response of the component to the heat source. In flowing thermography, a fluid (e.g., hotter or colder than the bulk temperature of the component) is flowed through internal passages of the component, and the thermal camera captures image data representative of the surface temperature of the component over time.

SUMMARY

The disclosure describes various techniques for non-destructively testing a component using thermography. In some examples, a tested component may be tested using flowing thermography. A thermal camera may capture image data during the flowing thermography test. A computing device may receive the image data and flow rate data measured by at least one flow meter during, prior to, or after the flowing thermography test. The computing device may associate flow values with the image data based on the flow rate data to generate quantitative flowing thermography image data. In this way, the image data captured by the thermal camera may provide quantitative indicators of the flow rate through internal passages of the tested component. The quantitative indicators may be used (e.g., by the computing device or a trained technician) to determine whether the flow of fluid through the internal passages is within or outside a predetermined range, e.g., a design range.

In some examples, a tested component may be tested using flowing thermography, flash thermography, or both. During the thermographic testing, the thermal camera may capture infrared data in the form of two-dimensional image data. In accordance with these examples, a computing device may receive the two-dimensional image data may morph the two-dimensional image data to substantially match master image data. The master image data may have been determined based on a fabricated gold standard component, or based on a nominal part geometry and material properties and a theoretical prediction of heat transfer for the nominal part geometry. The master image data may include a three-dimensional or two-dimensional representation of geometry of the gold standard component or the nominal part geometry, and may also include thermal response data of the gold standard component or determined based on a nominal part geometry and material properties and a theoretical prediction of heat transfer for the nominal part geometry. The computing device then may compare the two-dimensional image data to the master image data to determine any discrepancies between the morphed two-dimensional image data and the master image data. The computing device may compare any discrepancies to at least one threshold value, and, responsive to determining that a respective discrepancy is greater than or equal to the threshold value, the computing device may identify the respective discrepancy. In some examples, the computing device may output the morphed two-dimensional image data for display, e.g., as aligned with the geometry of the three-dimensional master component, and may highlight the respective discrepancies. This may facilitate identification of any discrepancies between the two-dimensional image data and the master image data, which may facilitate identification of deficiencies, such as defects, damage, blockages, or the like within the tested component.

In some examples, a single inspection station may include components that allow cleaning and flowing thermography testing of a component at the single inspection location. For example, a dry ice source may be used to introduce dry ice into the internal passages of the component to be cleaned. The dry ice may be introduced into the internal passages in solid form, such as powder, pellets, shavings, or the like, and may impact any debris within the internal passages, which may cause the debris to release from the walls of the internal passages and/or shatter into smaller pieces and be carried out of the internal passages with the dry ice.

In some examples, the dry ice may be used as to induce the temperature change in the component for flowing thermography, and the flowing thermography may be performed substantially simultaneously with the cleaning. In other examples, the system may include a fluid source, and the fluid may be used to perform flowing thermography on the component. Regardless of whether the dry ice or a fluid is used for flowing thermography, performing the cleaning and flowing thermography at a single inspection station may be more time and space efficient than utilizing two separate stations for the cleaning and the flowing thermography testing. Further, in examples in which dry ice is used to flowing thermography, cleaning and performing flowing thermography substantially simultaneously may be more time efficient that performing the procedures sequentially.

In an example, the disclosure describes a system including a fluid source fluidically coupled to a plenum, a thermal camera, at least one flow meter, and a computing device. In accordance with this example, the computing device is communicatively connected to the at least one flow meter and the thermal camera. The computing device may be configured to receive flow rate data from the at least one flow meter during flow testing of a first component fluidically coupled to the plenum, receive thermographic image data captured by the thermal camera during flowing thermographic testing of a second component fluidically coupled to the plenum, and associate the flow rate data to the thermographic image data to produce quantitative flowing thermographic image data.

In another example, the disclosure describes a method that includes receiving, by a computing device, from at least one flow meter, flow rate values relating to flow testing of a first component; receiving, by the computing device, from a thermal camera, thermographic image data captured by the thermal camera during flowing thermographic testing of a second component; and associating, by the computing device, the flow rate values with the thermographic image data to produce quantitative flowing thermographic image data.

In an additional example, the disclosure describes a computer readable storage medium comprising instructions that, when executed, cause at least one processor to receive, from at least one flow meter, flow rate values relating to flow testing of a first component; receive, from a thermal camera, thermographic image data captured by the thermal camera during flowing thermographic testing of a second component; and associate, the flow rate values with the thermographic image data to produce quantitative flowing thermographic image data.

In a further example, the disclosure describes a system including a thermal camera and a computing device. In accordance with this example, the computing device is configured to receive master image data representative of a geometry and thermal response of at least one of a theoretical component, a fabricated gold standard component, or an average of a plurality of components; receive, from the thermal camera, thermographic image data representative of a thermal response of a tested component; morph the thermographic image data to substantially align with the three-dimensional image data and produce morphed thermographic image data; and output a representation based on the morphed thermographic image data for display.

In another example, the disclosure describes a method including receiving, by a computing device, master image data representative of a geometry and thermal response of at least one of a theoretical component, a fabricated gold standard component, or an average of a plurality of components; receiving, by the computing device, from a thermal camera, thermographic image data representative of a thermal response of a tested component; morphing, by the computing device, the thermographic image data to substantially align with the three-dimensional image data and produce morphed thermographic image data; and outputting, by the computing device, a representation based on the morphed thermographic image data for display.

In a further example, the disclosure describes a computer readable storage medium comprising instructions that, when executed, cause at least one processor to receive master image data representative of a geometry and thermal response of at least one of a theoretical component, a fabricated gold standard component, or an average of a plurality of components; receive, from a thermal camera, thermographic image data representative of a thermal response of a tested component; morph the thermographic image data to substantially align with the three-dimensional image data and produce morphed thermographic image data; and output a representation based on the morphed thermographic image data for display.

In an additional example, the disclosure describes a system that includes a source of dry ice, a thermal camera, and a computing device. In accordance with this example, the computing device is configured to control the source of dry ice to cause dry ice to be introduced into an internal passage of a tested component. The tested component may include debris within the internal passage, and the dry ice may remove at least some of the debris from the internal passage. The computing device also may be configured to receive, from the thermal camera, thermographic image data representative of the thermal response of the tested component, and output a representation based on the thermographic image data.

In another example, the disclosure describes a method that includes controlling, by a computing device, a source of dry ice to cause dry ice to be introduced into an internal passage of a tested component. The tested component may include debris within the internal passage, and the dry ice may remove at least some of the debris from the internal passage. The method also may include receiving, by the computing device, from a thermal camera, thermographic image data representative of the thermal response of the tested component; and outputting, by the computing device, a representation based on the thermographic image data.

In an additional example, the disclosure describes a computer readable storage medium including instructions that, when executed, cause at least one processor to control a source of dry ice to cause dry ice to be introduced into an internal passage of a tested component. The tested component may include debris within the internal passage, and the dry ice may remove at least some of the debris from the internal passage. The computer readable storage medium may further include instructions that, when executed, cause the at least one processor to receive, from a thermal camera, thermographic image data representative of the thermal response of the tested component; and output a representation based on the thermographic image data.

The details of one or more examples are set forth in the accompanying drawings and the description below. Other features, objects, and advantages will be apparent from the description and drawings, and from the claims.

DETAILED DESCRIPTION

Figure 1:
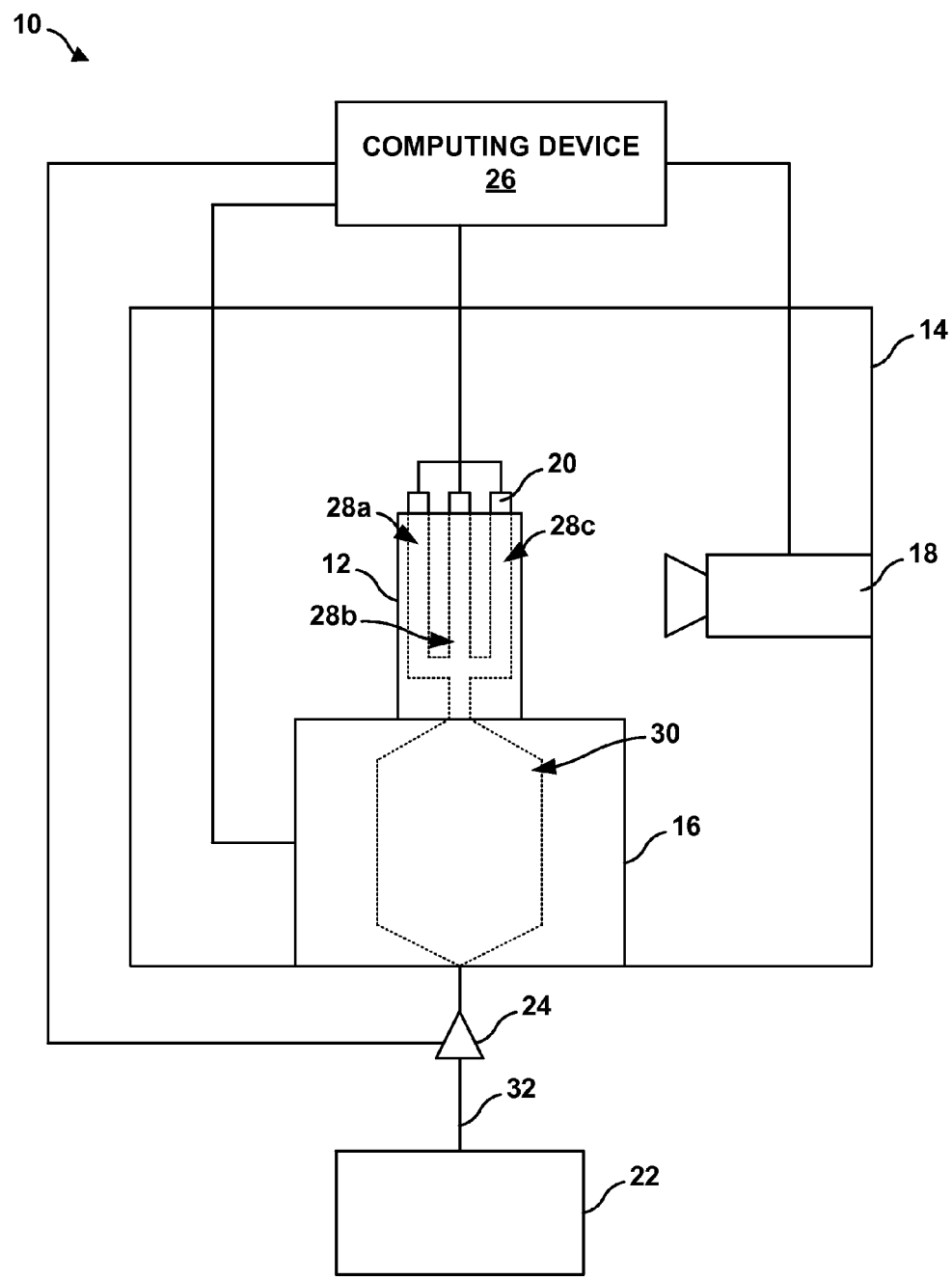
FIG. 1 is a conceptual block diagram illustrating an example system for performing flowing thermography on a tested component.

The disclosure describes various techniques for non-destructively testing a component using thermography. Thermography includes two types: flowing thermography and flash thermography. In flash thermography, a heat source, such as a flash lamp, is used to apply heat to the outer surface of the component. The thermal camera captures image data representative of the surface temperature of the component over time, which provides the thermal response of the component to the heat source. In flowing thermography, a fluid is flowed through internal passages of the component, and the thermal camera captures image data representative of the surface temperature of the component over time.

In some examples, the disclosure describes systems and techniques for producing quantitative flowing thermographic data, rather than qualitative flowing thermographic data. In conventional flowing thermography, data produced indicates a qualitative (e.g., relative) thermal response of different locations of the tested component (e.g., different exit orifices for the fluid flowing through the internal passages of the component). A trained technician, e.g., with knowledge of the nominal geometry and material properties of the tested component, may visually analyze the flowing thermography data to determine whether the tested component includes any deficiencies, such as blockages, defects, or damage in the internal passages of the component. However, this may be a time-consuming process and may require the technician to have extensive training and knowledge to accurately interpret the thermographic data.

To produce quantitative flowing thermographic data, a thermal camera may capture image data during the flowing thermography test for each of the plurality of locations (e.g., a plurality of pixels of a sensor of the thermal camera each capturing data for a corresponding location of the tested component). A computing device may receive the image data from the thermal camera. At least some of the locations (e.g., pixels) may correspond to an exit orifice of the tested component, through which the fluid used in flowing thermography can exit the tested component.

The computing device also may receive flow rate data measured by at least one flow meter prior to, during, or after the flowing thermography test. The flow rate data may include a flow rate for an exit orifice. The flow rate data may be produced using a fluid pulse with known flow rate. In some examples, the flow rate data includes respective flow rates for each of a plurality of exit orifices. In some examples, the flow rate data may be produced using a fabricated gold standard component (e.g., a component known to include no blocked or damaged internal passages and to correspond to nominal part geometry). In other examples, the flow rate data may be produced using a plurality of flow meters placed at respective exit orifices of the tested component.

The measured flow rate for an exit orifice may be correlated to the thermographic image data (e.g., at least one pixel) for a corresponding exit orifice (e.g., the same exit orifice or a location on the tested component at a location corresponding to that on the fabricated gold standard component) to associate flow rates with the thermographic image data. Based on a plurality of correlations between known flow rates and image data at corresponding exit orifices, the computing device may determine a relationship between the thermographic image data and flow rates. The computing device may associate flow values with pixels from the thermographic image data from the tested component based on the correlated flow rate data to form quantitative flowing thermography image data. In this way, the quantitative flowing thermography image data may provide quantitative indicators of the flow rate through internal passages of the tested component, rather than only qualitative (e.g., relative) flow rates through internal passages of the tested component. The quantitative indicators may be used (e.g., by the computing device or a trained technician) to determine whether the flow of fluid through the internal passages is within or outside a predetermined range, e.g., a design range.

In some examples, a tested component may be tested using flowing thermography, flash thermography, or both. During the thermographic testing, the thermal camera may capture infrared data in the form of two-dimensional thermographic image data. In accordance with these examples, a computing device may receive the two-dimensional thermographic image data and may morph the two-dimensional thermographic image data to substantially align (e.g., align or nearly align) with master image data. The master image data may have been determined based on testing of a fabricated gold standard component, testing of a plurality of components and generating a theoretical average component based on the plurality of components, or based on a nominal part geometry, material properties, and a theoretical prediction of fluid flow and heat transfer for the nominal part geometry. The master image data may include a three-dimensional or two-dimensional representation of geometry of the gold standard component, the nominal part geometry or the average geometry of the plurality of tested components, and may also include thermal response data of the gold standard component, the plurality of tested components, or determined based on a nominal part geometry and material properties and a theoretical prediction of heat transfer for the nominal part geometry.

The two-dimensional thermographic image data may not align with the master image data due to, for example, deviations in the geometry of the tested component from the nominal component geometry due to manufacturing variability, defects, damage, or the like. By morphing the two-dimensional thermographic image data to substantially align (e.g., align or nearly align) with the master image data, comparison between the measured thermal response and the thermal response of the fabricated gold standard component or theoretical thermal response of a nominal component may be facilitated and any deviations of the thermal response of tested component from the master image data may be easier to detect.

The computing device then may compare the two-dimensional thermographic image data to the master image data to determine any discrepancies between the morphed two-dimensional thermographic image data and the master image data. The computing device may perform the comparison on a per-pixel basis, or may aggregate a plurality of adjacent pixels into a set and perform the comparison on a per-set basis. The computing device may compare any discrepancies between the two-dimensional thermographic image data and the master image data to at least one threshold value, and, responsive to determining that a discrepancy is greater than or equal to the threshold value, the computing device may identify the respective discrepancy. In some examples, the computing device may output the morphed two-dimensional thermographic image data for display, e.g., as aligned to the geometry of the three-dimensional master component, and may highlight the respective discrepancies. This may facilitate identification of any discrepancies between the two-dimensional thermographic image data and the master image data, which may facilitate identification of deficiencies, such as defects, damage, blockages, or the like within the tested component.

In some examples, a single inspection station may include components that allow cleaning and flowing thermography testing of a component at the single inspection location. For example, a dry ice source may be used to introduce dry ice into internal passages of the component to be cleaned. The dry ice may be introduced into the internal passages in solid form and may impact any debris within the internal passages of the component, which may cause the debris to release from the walls of the internal passages and/or shatter into smaller pieces and be removed from the internal passages with the dry ice.

In some examples, the dry ice may be used to induce the temperature change in the component for flowing thermography, which may be performed substantially simultaneously with cleaning using the dry ice. In other examples, the system may include a fluid source, and the fluid may be used to perform flowing thermography on the component. Regardless of whether the dry ice or a fluid is used for flowing thermography, performing the cleaning and flowing thermography at a single inspection station may be more time and space efficient than utilizing two separate stations for the cleaning and the flowing thermography testing. Further, in examples in which dry ice is used for flowing thermography, cleaning and performing flowing thermography substantially simultaneously may be more time efficient that performing the procedures sequentially.

The various techniques described herein may be used together in different combinations. For example, the two-dimensional thermographic image data morphed to substantially align the master image data may include quantitative flowing thermographic image data and/or may include data generated using flowing thermography with dry ice. As another example, the quantitative flowing thermographic image data may be determined using thermographic data generated using dry ice. Other combinations of the techniques described herein are also contemplated by this disclosure and will be apparent to those of ordinary skill in the art.

FIG. 1 is a block diagram illustrating an example system 10 for performing flowing thermography on a tested component 12. System 10 includes an enclosure 14 defining an inspection station. Enclosure 14 encloses a stage 16 and a thermal camera 18. Also disposed within enclosure 14 is a plurality of flow meters 20. System 10 also includes a fluid source 22, which is fluidically coupled to stage 16 (e.g., a plenum 30 defined by stage 16). A valve 24 is located between fluid source 22 and stage 16. System 10 further includes a computing device 26, which may be communicatively coupled to stage 16, thermal camera 18, the plurality of flow meters 20, and/or valve 24.

System 10 includes components that allow both flow testing and flowing thermography testing at a single inspection station. This may facilitate generation of quantitative flowing thermography data, as described below. Additionally, this may simplify and speed performing flow testing and flowing thermography testing compared to examples in which flow testing and flowing thermography is performed at two separate and distinct inspection stations.

Figure 5:
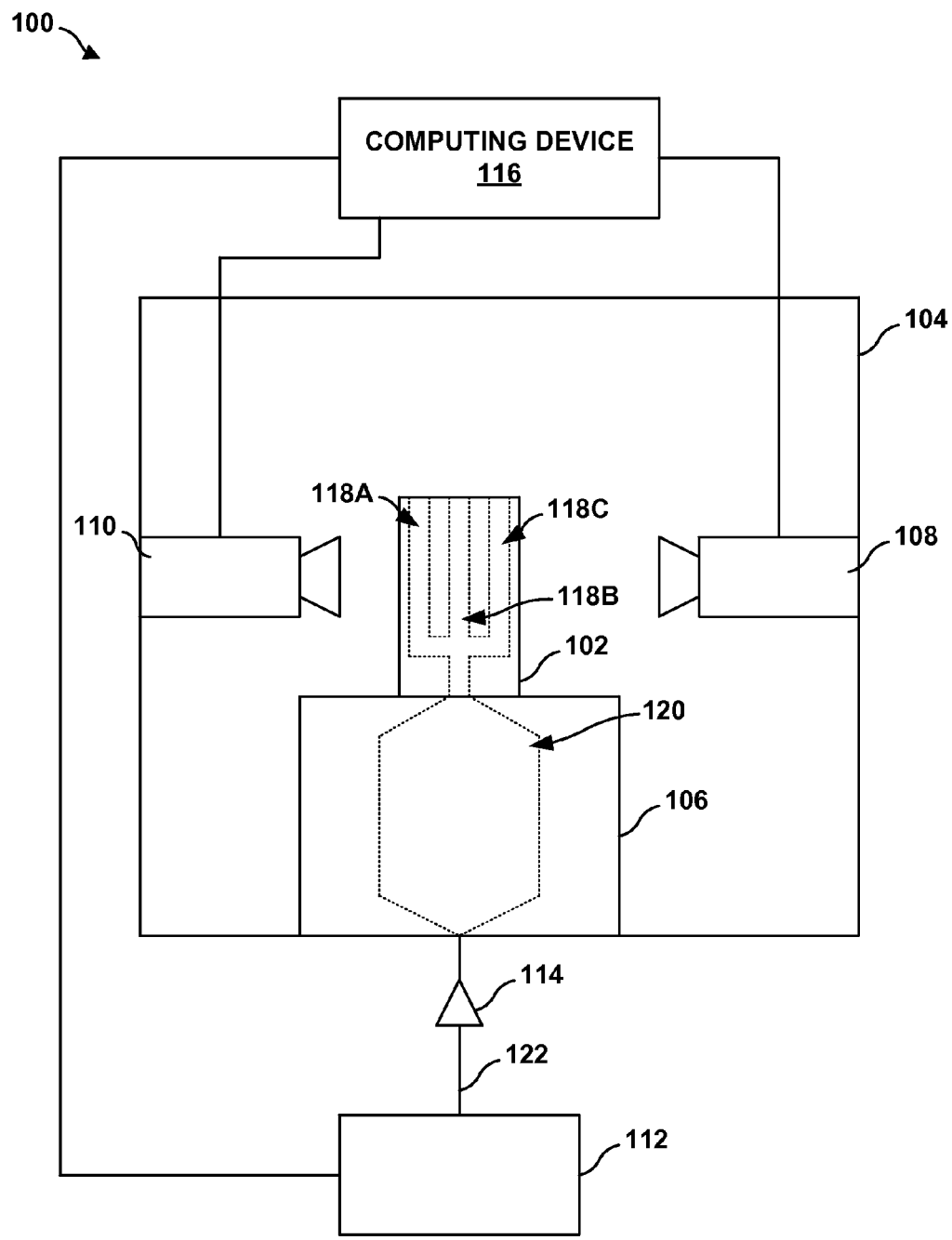
FIG. 5 is a conceptual block diagram illustrating an example system for performing flash thermography and flowing thermography on a tested component and morphing two-dimensional thermographic image data to substantially align with master image data.

Although not illustrated in FIG. 1, system 10 also may include a heat source (e.g., heat source 110 illustrated in FIG. 5). By including a heat source, system 10 also may be configured to perform flash thermography on tested component 12. In this way, in some examples, system 10 may be configured to perform flow testing, flowing thermography testing, and flash thermography on tested component 12 at a single inspection station.

System 10 may be used to inspect components 12 with internal passages 28 through which a fluid can flow. For example, system 10 may be used to inspect components with internal cooling passages and film cooling holes, such as gas turbine engine blades or vanes. Although tested component 12 is described herein as a gas turbine engine blade, it will be appreciated that system 10 and the technique described herein may be used to perform flow testing, flowing thermography, and generate quantitative flowing thermography data for other components including internal passages.

In some examples, stage 16 is movable relative to thermal camera 18 and/or thermal camera 18 is movable relative to stage 16. For example, stage 16 may be translatable and/or rotatable along at least one axis to position tested component 12 relative to thermal camera 18. Similarly, thermal camera 16 may be translatable and/or rotatable along at least one axis to position thermal camera 16 relative to tested component 12. In some examples, both stage 16 and thermal camera 18 are movable in at least one dimension. In other examples, only stage 16 or only thermal camera 18 is movable, and the other is substantially fixed in position.

Stage 16 may be configured to selectively position and restrain tested component 12 in place relative to stage 16 during testing of tested component 12. In some examples, stage 16 defines a plenum 30 for receiving fluid from fluid source 22. Stage 16 may define at least one aperture that is substantially aligned with at least one respective opening in tested component 12 when tested component 12 is positioned and restrained on stage 16. In this way, stage 16 may facilitate fluidic communication between tested component 12 and fluid source 22.

Thermal camera 18 includes an imaging device that produces a signal responsive to incident thermal radiation. In some examples, thermal camera 18 includes an infrared imaging device that detects infrared radiation. Thermal camera 18 may produce image data based on the signal, which may include data related to a plurality of pixels over time. The image data may be representative of a temperature of a corresponding location of tested component 12, e.g., a location of tested component 12 from which the respective pixel sensed thermal radiation over time. Thermal camera 18 may be communicatively coupled to computing device 26, e.g., via a wired or wireless communication connection (e.g., a USB connection, Ethernet connection, a wireless connection, or the like). Thermal camera 18 may communicate the image data to computing device 26 using the communication connection.

The plurality of flow meters 20 may include devices configured to detect a flow rate of fluid at the respective flow meters 20. The flow meters 20 may be configured to detect, for example, mass flow rate, volumetric flow rate, or the like. Flow meters 20 may be movable such that flow meters 20 may be positioned at predetermined locations of tested component 12. For example, flow meters 20 may be placed over or adjacent to exit orifices defined in tested component 12. Exit orifices may be apertures or orifices defined in tested component 12 and fluidically coupled to at least one internal passage 28 defined in tested component 12, through which fluid provided from fluid source 22 flows. In this way, flow meters 20 may be operable to detect fluid flow through a respective exit orifice. Flow meters 20 may be communicatively coupled to computing device 26 e.g., via a wired or wireless communication connection (e.g., a USB connection, Ethernet connection, a wireless connection, or the like). Flow meters 20 may communicate the flow data detected by the respective flow meters 20 to computing device 26.

Although not illustrated in FIG. 1, a flow meter may be disposed at a position along the fluid path from fluid source 22 to internal passages 28 (e.g., along fluid line 32, within plenum 30, or the like) to measure the flow rate of fluid entering into internal passages 28. This flow meter may be used to measure the flow rate of fluid entering into internal passages 28 during flow testing and/or flowing thermography.

Fluid source 22 includes a source of fluid, such as compressed air, for use during flowing thermography measurement and/or flow measurements. In some examples, fluid supply 22 may be configured to supply one or more liquids or other gases in addition to or in place of air. In some examples, fluid supply 22 is configured to supply cooled fluid to component 12. In other examples, fluid supply 22 may be configured to supply to component 12 a hot fluid and/or a room temperature fluid in addition to or in place of a cooled fluid. As shown in FIG. 1, fluid source 22 is fluidically coupled to plenum 30 defined by stage 16 by a fluid line 32. Fluid line 32 may include a pipe, conduit, tube, or the like. Valve 24 is controllable (e.g., by computing device 26) to open and close to control a flow rate of fluid from fluid source 22 to plenum 30.

Computing device 26 may include, for example, a desktop computer, a laptop computer, a workstation, a server, a mainframe, a cloud computing system, or the like. Computing device 26 is configured to control operation of system 10, including, for example, stage 16, thermal camera 18, flow meters 20, and/or valve 24. Computing device may be communicatively coupled to at least one of stage 16, thermal camera 18, flow meters 20, or valve 24 using respective communication connections. In some examples, the communication connections may include network links, such as Ethernet, ATM, or other network connections. Such connections may be wireless and/or wired connections. In other examples, the communication connections may include other types of device connections, such as USB, IEEE 1394, or the like.

Computing device 26 may be configured to control operation of stage 16 and/or thermal camera 18 to position tested component 12 relative to thermal camera 18. For examples, as described above, computing device 26 may control stage and/or thermal camera 18 to translate and/or rotate along at least one axis to position tested component 12 relative to thermal camera 18. Positioning tested component 12 relative to thermal camera 18 may include positioning a predetermined surface of tested component 12 to be imaged using thermal camera 18.

Computing device 26 also may be configured to control valve 24 to open and close to allow fluid to flow from fluid source 22 to plenum 30 and stop fluid flow from fluid source 22 to plenum 30. In this way, computing device 26 may cause a predetermined amount of fluid to flow over a predetermined duration to produce a predetermined flow rate of fluid from fluid source 22.

In accordance with some examples of this disclosure, computing device 26 may be configured to receive data from thermal camera 18 and/or respective flow meters 20 and correlate the data to produce quantitative flowing thermography data. In some examples, computing device 22 may be configured to receive flow data from the respective flow meters 20 may be representative of a flow rate of fluid detected by the respective flow meters 20. During flow tests, fluid, e.g., provided by fluid source 22 may flow through internal passages 28 of tested component 12. For example, computing device 26 may control valve 24 to open a predetermined amount for a predetermined duration to cause a predetermine amount of fluid to be released from fluid source 22. The predetermined amount of fluid may flow through fluid line 32 to plenum 30, then through internal passages 28 and out the exit orifices defined in component 12 (e.g., with flow meters 20 removed from component 12). Flow meters 20 may detect the fluid flow passing by each respective flow meter 20, and communicate data representative of the fluid flow to computing device 26. Computing device 26 may associate the flow data of each flow meter 20 with a respective orifice defined in tested component 12 (e.g., specific location of tested component 12).

Computing device 26 also may be configured to receive thermographic image data from thermal camera 18. The thermographic image data may include data for respective pixels from a sensor of thermal camera 18. Each pixel data may include intensity and/or wavelength over time, representative of a temperature of the location from which the pixel is sensing thermal radiation (e.g., a location on tested component 12). The thermographic image data may thus represent the temperature of at least a portion of tested component 12 over time.

In flowing thermography, fluid, e.g., provided by fluid source 22 may flow through internal passages 28 of tested component 12. For example, computing device 26 may control valve 24 to open a predetermined amount for a predetermined duration to cause a predetermine amount of fluid to be released from fluid source 22 (e.g., a pulse of fluid). The predetermined amount of fluid may flow through fluid line 32 to plenum 30, then through internal passages 28 and out the exit orifices defined in component 12 (e.g., with flow meters 20 removed from component 12). The flowing fluid may produce a transient temperature change of tested component 12 from an equilibrium temperature (e.g., the temperature of the surrounding atmosphere). As the pulse of fluid flows through internal passages 28 and out through the corresponding orifices, thermal camera 18 may capture data representative of the temperature of the surface of tested component 12, with each individual sensor (e.g., corresponding to a pixel) capturing data representative of the temperature of particular location of tested component 12 over time.

Computing device 26 may be configured to receive the data representative of the temperature of the surface of tested component 12 (thermographic image data) and process the data to produce thermographic image data suitable for further manipulation, such as outputting as a visual representation for display at a display device or correlating with the flow data measured by the flow meters 20. For example, computing device 26 may be configured to assign false color values or relative grayscale values to respective intensity and/or wavelength values in the thermographic image data, such that the relative intensity and/or wavelength may be perceived by a user viewing the visual representation.

In some examples, computing device 26 may determine a single value representative of the thermal response of a location of tested component 12 (e.g., represented by a pixel or a set of adjacent pixels) over a duration of time. For example, the duration may be from the initial change in temperature of the location from the equilibrium temperature until the location returns to the equilibrium temperature. The single value may incorporate at least one attribute of the thermal response of the location, including, for example, maximum temperature, minimum temperature, rate of temperature change, time to return to equilibrium temperature, or the like.

The thermographic image data, without more, may provide a relative indication of the fluid flow out of respective orifices of tested component 12. However, a trained technician then may need to view and interpret the visual representation to determine whether the thermographic image data indicates that any of the flow rates out of the orifices are out-of-specification, e.g., due to blockage, damage, or defect. This may require significant training and technician time to interpret the thermographic imaging data, and also may leave room for technician error in interpreting the visual representation.

In accordance with some examples, computing device 26 may be configured to correlate flow data received from flow meters 20 and thermographic image data received from thermal camera 18 to associate flow values with the thermographic image data to produce quantitative flowing thermographic image data. For example, computing device 26 may associate flow values determined for respective orifices at which a respective one of flow meters 20 were positioned with thermographic image data values for the respective orifices. By performing this correlation, computing device 26 may associate different flow values with different thermographic image data values, and may determine a relationship between flow values and thermographic image data values. Computing device 26 then may use this relationship to associate flow values with thermographic image data values for other locations of tested component 12.

Hence, computing device 26 may be configured to associate quantitative flow rate values to thermographic image data to produce quantitative flowing thermographic image data. Quantitative flowing thermographic image data may facilitate determination, e.g., by computing device 26 or a technician, of whether flow rates from respective orifices are within specification. For example, the specification may define flow rate values for respective orifices in response to a predefined flow into internal passages 28. The flow rates of respective orifices from the quantitative flowing thermographic image data may be compared (e.g., by computing device 26 or a technician) to the respective defined flow rate values to determine whether the measured flow rates are within specification or outside of specification (e.g., due to damage, defect, blockages, or the like).

Figure 2:
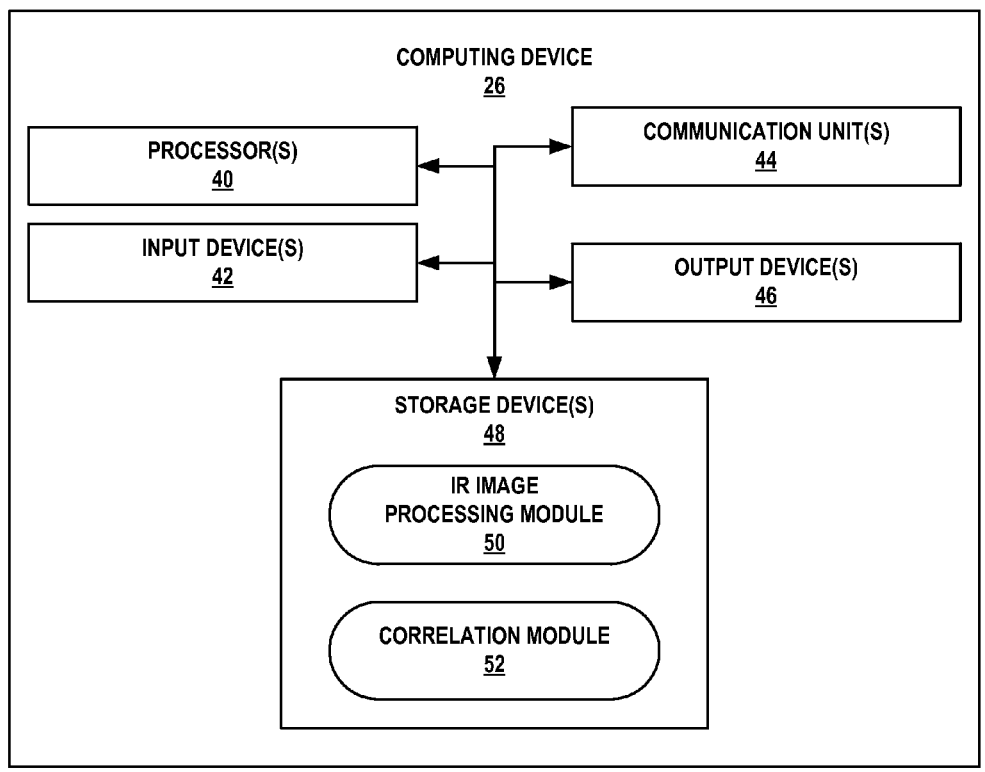
FIG. 2 is a conceptual block diagram illustrating an example of a computing device.

FIG. 2 is a conceptual block diagram illustrating an example of computing device 26 illustrated in FIG. 1. In the example illustrated in FIG. 2, computing device 26 includes one or more processors 40, one or more input devices 42, one or more communication units 44, one or more output devices 46, and one or more storage devices 48. In some examples, one or more storage devices 48 stores thermographic image processing module 50 and correlation module 52. In other examples, computing device 26 may include additional components or fewer components than those illustrated in FIG. 2.

One or more processors 40 are configured to implement functionality and/or process instructions for execution within computing device 26. For example, processors 40 may be capable of processing instructions stored by storage device 48. Examples of one or more processors 40 may include, any one or more of a microprocessor, a controller, a digital signal processor (DSP), an application specific integrated circuit (ASIC), a field-programmable gate array (FPGA), or equivalent discrete or integrated logic circuitry.

One or more storage devices 48 may be configured to store information within computing device 26 during operation. Storage devices 48, in some examples, include a computer-readable storage medium or computer-readable storage device. In some examples, storage devices 48 include a temporary memory, meaning that a primary purpose of storage device 48 is not long-term storage. Storage devices 48, in some examples, include a volatile memory, meaning that storage device 48 does not maintain stored contents when power is not provided to storage device 48. Examples of volatile memories include random access memories (RAM), dynamic random access memories (DRAM), static random access memories (SRAM), and other forms of volatile memories known in the art. In some examples, storage devices 48 are used to store program instructions for execution by processors 40. Storage devices 48, in some examples, are used by software or applications running on computing device 26 to temporarily store information during program execution.

In some examples, storage devices 48 may further include one or more storage device 48 configured for longer-term storage of information. In some examples, storage devices 48 include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

Computing device 26 further includes one or more communication units 44. Computing device 26 may utilize communication units 44 to communicate with external devices (e.g., stage 16, thermal camera 18, flow meters 20, and/or valves 24) via one or more networks, such as one or more wired or wireless networks. Communication unit 44 may be a network interface card, such as an Ethernet card, an optical transceiver, a radio frequency transceiver, or any other type of device that can send and receive information. Other examples of such network interfaces may include WiFi radios or Universal Serial Bus (USB). In some examples, computing device 26 utilizes communication units 44 to wirelessly communicate with an external device such as a server.

Computing device 26 also includes one or more input devices 42. Input devices 42, in some examples, are configured to receive input from a user through tactile, audio, or video sources. Examples of input devices 42 include a mouse, a keyboard, a voice responsive system, video camera, microphone, touchscreen, or any other type of device for detecting a command from a user.

Computing device 26 may further include one or more output devices 46. Output devices 46, in some examples, are configured to provide output to a user using audio or video media. For example, output devices 46 may include a display, a sound card, a video graphics adapter card, or any other type of device for converting a signal into an appropriate form understandable to humans or machines.

Computing device 26 also may include thermographic image processing module 50 and correlation module 52. Thermographic image processing module 50 and correlation module 52 may be implemented in various ways. For example, thermographic image processing module 50 and/or correlation module 52 may be implemented as an application executed by one or more processors 40. In other examples, thermographic image processing module 50 and/or correlation module 52 may be implemented as part of a hardware unit of computing device 20 or as part of an operating system provided by computing device 20. Functions performed by thermographic image processing module 50 and correlation module 52 are explained below with reference to the example flow diagrams illustrated in FIGS. 3 and 4.

Computing device 26 may include additional components that, for clarity, are not shown in FIG. 2. For example, computing device 26 may include a power supply to provide power to the components of computing device 26. Similarly, the components of computing device 26 shown in FIG. 2 may not be necessary in every example of computing device 26.

Figure 3:
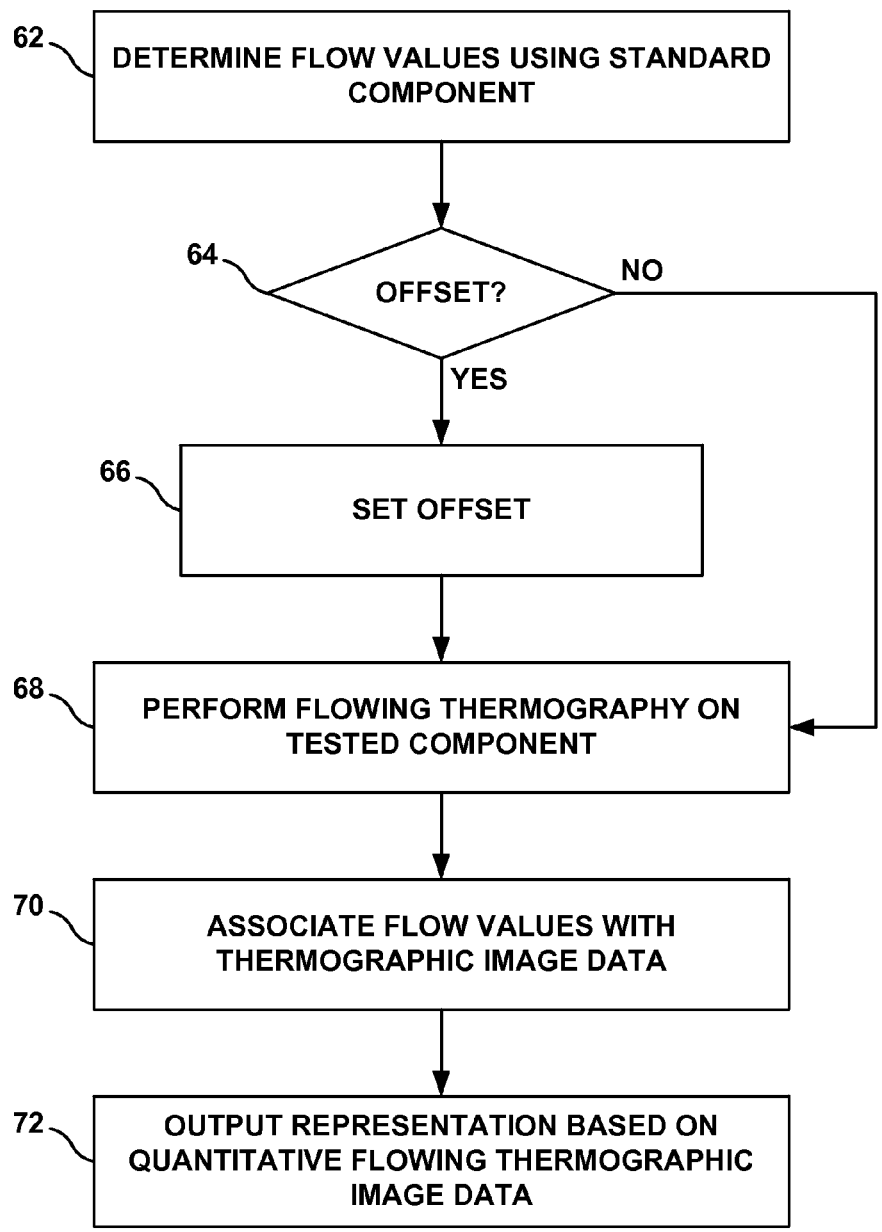
FIG. 3 is a flow diagram illustrating an example technique for associating flow values measured using a fabricated gold standard component with flowing thermographic image data.

In accordance with some examples of the disclosure, computing device 26 can be configured to receive flow data from flow meters 20, receive thermographic image data from thermal camera 18, and generate quantitative flowing thermographic image data by associating flow values with thermographic image data. FIG. 3 is a flow diagram illustrating an example technique for associating flow values measured using a fabricated gold standard component with flowing thermographic image data. Although the technique of FIG. 3 will be described with respect to system 10 of FIG. 1 and computing device 26 of FIG. 2, in other examples, the technique of FIG. 3 may be performed using a different system. Additionally, system 10 and computing device 26 may perform other techniques to associate flow values with flowing thermographic image data (e.g., the technique illustrated in FIG. 4).

The technique illustrated in FIG. 3 includes determining at least one flow value using at least one flow meter 20 adjacent to at least one respective exit orifice of a fabricated gold standard component (62). The fabricated gold standard component may be positioned on and restrained with respect to stage 16, similar to tested component 12 illustrated in FIG. 1. The fabricated gold standard component may be a component known to include no blocked or damaged internal passages and to correspond to nominal part geometry. The fabricated gold standard component also may have a geometry substantially similar to tested component 12 (e.g., the same aside from any damage, defects, blockages, or deviation from design specifications in tested component 12). As described above, in some examples, the component may include a gas turbine component, such as a gas turbine engine blade or vane. In some examples, internal passages 28 may include internal cooling channels, and the exit orifices may include film cooling holes. In such examples, the fabricated gold standard component may define a geometry corresponding to the nominal (e.g., designed) blade or vane geometry, and may include no blocked or damaged internal cooling channels and film cooling holes.

As shown in FIG. 1, flow meters 20 may be placed adjacent to the exit orifices to measure fluid flow exiting the respective exit orifices. Although three flow meters 20 are depicted in FIG. 1, in other examples, fewer or more flow meters 20 may be used to measure flow values. The respective flow values may represent a flow rate out of a corresponding one of the exit orifices, which may be representative of the flow rate through the internal passage fluidically coupled to the exit orifice.

To measure the flow values, computing device 26 (e.g., one or more processors 40 executing instructions) may control valve 24 to open a predetermined amount for a predetermined duration to cause a predetermine amount of fluid to be released from fluid source 22. The predetermined amount of fluid may flow through fluid line 32 to plenum 30, then through internal passages 28 and out the exit orifices defined in component 12 (e.g., with flow meters 20 removed from component 12). Flow meters 20 may detect the fluid flow passing by each respective flow meter 20, and communicate data representative of the fluid flow to computing device 26. Computing device 26 may associate the flow data of each flow meter 20 with a respective exit orifice defined in the fabricated gold standard component (e.g., a specific location of the fabricated gold standard component).

The technique of FIG. 3 also includes determining whether an offset to the flow values should be used (64). The offset may be used when conditions specific to the day (e.g., temperature in the system 10, pressure within fluid source 22, ambient pressure, or the like) cause the flow values to be different than they would otherwise be on a different day (e.g., a day with a different temperature or pressure). Responsive to computing device 26 determining that an offset should be used, computing device 26 may set the offset (66) and apply the offset to the measured flow values. Responsive to computing device 26 determining that an offset should not be used, computing device 26 may not set the offset, but may instead proceed to begin thermographic inspection of tested component 12 (68).

After flow testing of the fabricated gold standard component, the fabricated gold standard component may be removed from stage 16, and tested component 12 may be positioned and restrained on stage 16. The technique of FIG. 3 then includes performing flowing thermography on tested component 12 (68). During flowing thermography, computing device 26 may be configured to control valve 24 to open a predetermined amount for a predetermined duration to cause a predetermine amount of fluid to be released from fluid source 22 during the predetermined duration (e.g., a pulse of fluid). In some examples, the amount of fluid and flow rate entering into internal passages 28 through plenum 30 during flowing thermography may be the same as the amount of fluid and flow rate entering into internal passages 28 through plenum 30 during flow rate measurement.

The predetermined amount of fluid may flow through fluid line 32 to plenum 30, then through internal passages 28 and out the exit orifices defined in component 12 (e.g., with flow meters 20 removed from component 12). The flowing fluid may produce a transient temperature change of tested component 12 from an equilibrium temperature (e.g., the temperature of the surrounding atmosphere). As the pulse of fluid flows through internal passages 28 and out through the corresponding orifices, thermal camera 18 may capture data representative of the temperature of the surface of tested component 12, with each individual sensor (e.g., corresponding to a pixel) capturing data representative of the temperature of particular location of tested component 12 over time.

Computing device 26 and, more particularly, thermographic image processing module 50, may be configured to receive the data representative of the temperature of the surface of tested component 12 (thermographic image data) and process the thermographic image data to produce a type of data suitable for further manipulation, such as outputting as a visual representation of the thermographic image data or associating with flow values based on the measured flow values from the fabricated gold standard component. For example, thermographic image processing module 50 may be configured to assign false color values or grayscale values to respective pixels in the thermographic image data based on the intensity and/or wavelength of the sensed by a pixel over time, such that the relative sensed intensity and/or wavelength may be perceived by a user viewing the visual representation.

In some examples, thermographic image processing module 50 may determine a single value representative of the thermal response of a location of tested component 12 over a duration of time. In some examples, thermographic image processing module 50 may be configured to group a plurality of adjacent pixels, e.g., based on a similar thermal response, and determine a single value representative of the average thermal response of the group of adjacent pixels over the duration of time. In other examples, thermographic image processing module 50 may be configured to, for each individual pixel, determine a single value representative of the thermal response of the respective pixel over the duration of time. In some examples, the duration may begin at the initial change in temperature of the location from the equilibrium temperature and end at the time the location approximately returns to the equilibrium temperature.

The single value for the thermal response of a pixel or a group of pixels during the duration of time may incorporate at least one attribute of the thermal response of the location. The at least one attribute of the thermal response of the location may include, for example, the maximum temperature (e.g., represented by maximum detected intensity and/or detected wavelength), minimum temperature (e.g., represented by maximum detected intensity and/or detected wavelength), rate of temperature change (e.g., represented by rate of change in detected intensity and/or rate of change of detected wavelength), time to return to equilibrium temperature, or the like. In some examples, thermographic image module 26 may determine the single value for the thermal response of the pixel or group of pixels based on only one of these attributes, while in other examples, thermographic image module 26 may determine the single value for the thermal response of the pixel or group of pixels based on a weighted combination of at least two attributes. Thermographic image module 26 may determine the single value for each pixel or each group of pixels that make up the thermographic image data. Thermographic image processing module 50 then may assign respective false color values or respective grayscale values to each determined single value. In this way, computing device may produce thermographic image data, which is suitable for further manipulation, such as outputting for display at a display device or associating with quantitative flow values.

The technique of FIG. 3 also include associating, by correlation module 52, flow numbers to the thermographic image data based at least in part on flow values from the fabricated gold standard component (70). For example, correlation module 52 may be configured to associate flow values determined for respective exit orifices at which a respective one of flow meters 20 were positioned with thermographic image data values (e.g., single values) for the respective exit orifices. By performing this correlation, correlation module 52 may associate different flow values with different thermographic image data values (e.g., single values), and may determine a relationship between flow values and thermographic image data values. Correlation module 52 then may use this determined relationship to associate flow values with thermographic image data values for other locations of tested component 12 (e.g., other single values for respective pixels or groups of pixels).

In this way, computing device 26 may be configured to associate quantitative flow rate values to thermographic image data to produce quantitative flowing thermographic image data. Quantitative flowing thermographic image data may facilitate determination, e.g., by computing device 26 or a technician, of whether flow rates from respective exit orifices are within specification. For example, the specification may define flow rate values for respective exit orifices in response to a predefined flow into internal passages 28. The flow rates of respective exit orifices from the quantitative flowing thermographic image data may be compared (e.g., by computing device 26 or a technician) to the respective defined flow rate values to determine whether the measured flow rates are within specification or outside of specification (e.g., due to damage, defect, blockages, or the like).

In some examples, correlation module 52 may be configured to assign respective false color values or respective grayscale values to each flow value. Correlation module 52 then may be configured to output a visual representation based on the quantitative flowing thermographic image data for display at a display (e.g., one or more output devices 46) (72). For example, correlation module 52 may be configured to output the flow values as a function of position. This may allow a user to visually perceive the quantitative flowing thermographic image data as a function of position on tested component 12, which may facilitate analysis of the quantitative flowing thermographic image data to determine if flow rates at various locations of tested component 12 are within specification.

Figure 4:
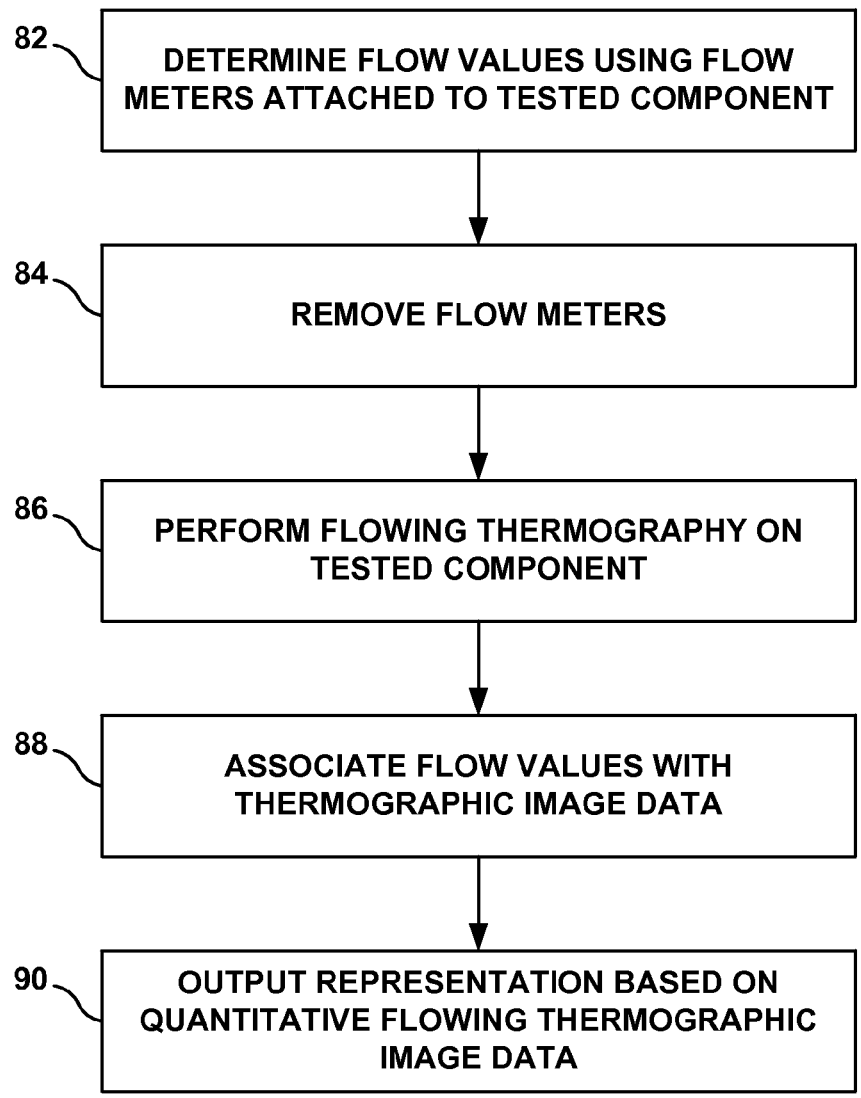
FIG. 4 is a flow diagram illustrating an example technique for associating flow values measured using the tested component with flowing thermographic image data.

Although a fabricated gold standard component is used to determine flow rates in the example illustrated in FIG. 3, in other examples, a fabricated gold standard component may not be utilized and flow rates may be determined at respective locations of tested component 12. FIG. 4 is another flow diagram illustrating an example technique for associating flow values determined using tested component 12 with flowing thermographic image data. Although the technique of FIG. 4 will be described with respect to system 10 of FIG. 1 and computing device 26 of FIG. 2, in other examples, the technique of FIG. 4 may be performed using a different system. Additionally, system 10 and computing device 26 may perform other techniques to associate flow values to flowing thermographic image data (e.g., the technique illustrated in FIG. 3).

The technique of FIG. 4 includes determining flow values using flow meters 20 attached to tested component 12 adjacent to respective exit orifices (82). As described above, in some examples, tested component 12 may include a gas turbine component, such as a gas turbine engine blade or vane. In some examples, internal passages 28 may include internal cooling channels, and the exit orifices may include film cooling holes.

As shown in FIG. 1, flow meters 20 may be placed adjacent to the exit orifices to measure fluid flow exiting the respective exit orifices. Although three flow meters 20 are depicted in FIG. 1, in other examples, fewer or more flow meters 20 may be used to measure flow values. The respective flow values may represent a flow rate out of a corresponding one of the exit orifices, which may be representative of the flow rate through the internal passage fluidically coupled to the exit orifice.

To measure the flow values, computing device 26 (e.g., one or more processors 40 executing instructions) may control valve 24 to open a predetermined amount for a predetermined duration to cause a predetermine amount of fluid to be released from fluid source 22. The predetermined amount of fluid may flow through fluid line 32 to plenum 30, then through internal passages 28 and out the exit orifices defined in component 12 (e.g., with flow meters 20 removed from component 12). Flow meters 20 may detect the fluid flow passing by each respective flow meter 20, and communicate data representative of the fluid flow to computing device 26. Computing device 26 may associate the flow data of each flow meter 20 with a respective exit orifice defined in tested component 12. After flowing the fluid through internal passages 28 and determining the flow values (82), flow meters 20 may be removed from adjacent to the exit orifices, leaving the exit orifices uncovered.

The technique of FIG. 4 also includes performing flowing thermography on tested component 12 (86). This step may be similar to or substantially the same as step (68) described with respect to FIG. 3. The technique of FIG. 4 then may include associating, by correlation module 52, flow values to the thermographic image data produced by flowing thermography based on flow values measured using flow meters 20 (88). For example, correlation module 52 may be configured to associate flow values determined for respective exit orifices at which a respective one of flow meters 20 were positioned with thermographic image data values (e.g., single values) for the respective exit orifices. By performing this correlation, correlation module 52 may associate different flow values with different thermographic image data values (e.g., single values), and may determine a relationship between flow values and thermographic image data values. Correlation module 52 then may use this determined relationship to associate flow values with thermographic image data values for other locations of tested component 12 (e.g., other single values for respective pixels or groups of pixels).

In this way, computing device 26 may be configured to associate quantitative flow rate values to thermographic image data to produce quantitative flowing thermographic image data. Quantitative flowing thermographic image data may facilitate determination, e.g., by computing device 26 or a technician, of whether flow rates from respective exit orifices are within specification. For example, the specification may define flow rate values for respective exit orifices in response to a predefined flow into internal passages 28. The flow rates of respective exit orifices from the quantitative flowing thermographic image data may be compared (e.g., by computing device 26 or a technician) to the respective defined flow rate values to determine whether the measured flow rates are within specification or outside of specification (e.g., due to damage, defect, blockages, or the like).

In some examples, correlation module 52 may be configured to assign respective false color values or respective grayscale values to each flow value. Correlation module 52 then may be configured to output a visual representation based on the quantitative flowing thermographic image data for display at a display (e.g., one or more output devices 46) (90). For example, correlation module 52 may be configured to output the flow values as a function of position. This may allow a user to visually perceive the quantitative flowing thermographic image data as a function of position on tested component 12, which may facilitate analysis of the quantitative flowing thermographic image data to determine if flow rates at various locations of tested component 12 are within specification.

As described above, in some examples, the disclosure describes techniques for morphing two-dimensional thermographic image data to substantially align with master image data. The thermographic image data may be produced using flowing thermography, flash thermography, or both. A computing device may receive the two-dimensional thermographic image data and may morph the two-dimensional thermographic image data to substantially align with master image data. FIG. 5 is a conceptual block diagram illustrating an example system 100 for performing flash thermography and flowing thermography on a tested component and morphing two-dimensional thermographic image data to substantially align with master image data.

In some examples, system 100 may be similar to or substantially the same (e.g., the same or nearly the same) as system 10 described with reference to FIG. 1. For example, like system 10, system 100 includes an enclosure 104, a stage 106, a thermal camera 108, a fluid source 112, a valve 114, a computing device 116, and a flow line 122. These components may be similar to or substantially the same as the corresponding components described with respect to FIG. 1. For example, stage 106 may be movable (e.g., translatable and/or rotatable) in at least one dimension and/or thermal camera 108 may be movable (e.g., translatable and/or rotatable) in at least one dimension to position tested component 102 with respect to thermal camera 108. Similarly, stage 106 may define a plenum 120, which is fluidly connected to fluid line 122 and internal passages 118 of component 102 when component 102 is positioned on and restrained with respect to stage 106.

Unlike system 10 of FIG. 1, in some examples, system 100 of FIG. 5 may not include a flow meter. However, in other examples, system 100 may include at least one flow meter. Also unlike system 10, system 100 may include a heat source 110. Heat source 110 may be controlled by computing device 106, and may be configured to generate a pulse of heat to a surface of tested component 102. In some examples, heat source 110 may include a flash lamp or an infrared heat source.

In this way, in some examples, system 100 may be configured to perform both flowing thermography and flash thermography at a single testing location. In other examples, system 100 may include heat source 110 and may not include fluid source 112, fluid line 122, and valve 114, such that system 100 is configured to perform flash thermography and not flowing thermography. In still other examples, system 100 may not include heat source 110 and may include fluid source 112, fluid line 122, and valve 114, such that system 100 is configured to perform flowing thermography and not flowing thermography.

Regardless of whether system 100 is configured to perform flash thermography, flowing thermography, or both, computing device 116 is configured to receive thermographic image data from thermal camera 108. As described above, thermographic image data may include data for respective pixels from a sensor of thermal camera 108. The data for each pixel may include intensity and/or wavelength over time, representative of a temperature of the location from which the pixel is sensing thermal radiation (e.g., a location on tested component 102). The thermographic image data may thus represent the temperature of at least a portion of tested component 102 over time.

In some examples, computing device 116 may determine a single value representative of the thermal response of a location of tested component 102 (e.g., represented by a pixel or a set of adjacent pixels) over a duration of time. For example, the duration may be from the initial change in temperature of the location from the equilibrium temperature until the location returns to the equilibrium temperature. The single value may incorporate at least one attribute of the thermal response of the location, including, for example, maximum temperature, minimum temperature, rate of temperature change, time to return to equilibrium temperature, or the like.

In some examples, the thermographic image data may be in a format corresponding to a two-dimensional array, as the sensor elements of thermal camera 108 may be arranged in a two-dimensional array. However, the two-dimensional array represents thermographic image data from a portion of three-dimensional component 102, which is a three-dimensional object. In some examples, the thermographic image data include concatenated image data from a plurality of thermography tests. For example, a first thermography test may be performed with component 102 positioned in a first orientation relative to thermal camera 108. Component 102 then may be moved relative to thermal camera 108 to orient a different surface or a different portion of a surface of component 102 toward thermal camera 108. A second thermography test may be performed. This procedure may be repeated until a predetermined portion of component 102 (e.g., all exposed surfaces of component 102) have been imaged.

In some examples, computing device 116 may be configured to combine a plurality of sets of thermographic image data into a single set representative of the thermographic response of component 102. For example, each set of thermographic image data may be associated with a set of coordinates representative of the orientation of component 102 relative to thermal camera 108. Computing device 116 may be configured to combine the plurality of sets of thermographic image data based on the coordinates of the respective sets of thermographic image data. In other examples, computing device 116 may be configured to perform one or more image recognition techniques to recognize similar features (e.g., representative of the same exit orifice) in two sets of thermographic image data and combine the two sets of thermographic image data based on the similar features.

Computing device 116 also may store and/or receive master image data. The master image data may be representative of three-dimensional geometry and thermal response of a theoretical component, a fabricated gold standard component, or an average geometry and thermal response of a plurality of tested components 102. For example, a theoretical component may be defined in a CAD/CAM file as a set of coordinates corresponding to points on the surfaces of the theoretical component. In some examples, the theoretical component may define a nominal or design geometry of tested component 102. That is, the theoretical component may define the geometry that tested component 102 was designed to possess. However, the actual geometry of tested component 102 may depart from the geometry of the theoretical component due to manufacturing tolerances, damage, wear, defects, or the like.

The thermal response and fluid flow characteristics of the theoretical component may also be determined using modeling. For example, based on the nominal geometry and theoretical properties of the material(s) from which the theoretical component is formed (e.g., heat transfer coefficients and the like), the thermal response of the theoretical component may be predicted using computer modeling, such as finite element analysis. The three-dimensional master data may include data representative of the geometry of the theoretical component (e.g., a set of coordinates defining surfaces of the fabricated gold standard component) and the thermal response of the theoretical component. In some examples, the thermal response of the theoretical component may be theoretically determined using the a model of the same type of thermography used to inspect tested component 102 and/or a model of the same parameters (e.g., temperature and flow rate of the fluid pulse for flowing thermography or intensity of radiation in flash thermography) used to inspect tested component 102.

Similarly, the fabricated gold standard component may define a geometry substantially the same (e.g., the same or nearly the same) as the nominal or design geometry of tested component 102. The thermal response of the fabricated gold standard component may be determined using flowing thermography and/or flash thermography. The three-dimensional master data may include data representative of the geometry of the fabricated gold standard component (e.g., a set of coordinates defining surfaces of the fabricated gold standard component) and the thermal response of the fabricated gold standard component. In some examples, the thermal response of the fabricated gold standard component may be determined using the same type of thermography used to inspect tested component 102 and/or the same parameters (e.g., temperature and flow rate of the fluid pulse for flowing thermography or intensity of radiation in flash thermography) used to inspect tested component 102.

In other examples, the master data may be determined based on geometric data and thermography results from a plurality of tested components 102. For example, computing device 116 may receive geometric data from a plurality of tested components 102 and may determine an average geometry and dimensional tolerances based on the geometric data. Computing device 116 also may receive flow data for the plurality of tested components 102 and/or thermographic image data for the plurality of tested components 102 and may determine average flow characteristics and thermographic image data for the plurality of components 102 and tolerances for the flow data and thermographic image data. These averages and tolerances (geometric, flow, and/or thermographic image) then may then constitute the master image data.

Computing device 116 may be configured to morph (e.g., translate, rotate, scale, and/or stretch) the thermographic image data to substantially align (e.g., align or nearly align) with the master image data. For example, computing device 116 may be configured to morph the thermographic image data so that each location of component 102 represented in the thermographic image data substantially aligns (e.g., aligns or nearly aligns) with a respective location represented in the master image data.

In some examples, portions of the thermographic image data may be associated with respective sets of coordinates representative of the orientation of component 102 relative to thermal camera 108, such that individual geometric features of component 102 are associated with sets of coordinates (e.g., each exit orifice may be associated with a respective set of coordinates). Similarly, portions of the master image data may be associated with respective sets of coordinates representative of the orientation of the fabricated gold standard component relative to thermal camera 108 or representative of a theoretical orientation of the theoretical component to a theoretical thermal camera, such that individual geometric features of the fabricated gold standard component or theoretical component are associated with sets of coordinates (e.g., each exit orifice may be associated with a respective set of coordinates). Computing device 116 may be configured to utilize the sets of coordinates for the thermographic image data and the sets of coordinates associated with the master image data to perform a first morphing operation (e.g., including translating, rotating, scaling, and/or stretching the thermographic image data) and roughly align the thermographic image data to the master image data.

In some examples, computing device 106 may be configured to perform multiple, progressively more precise image morphing manipulations. For example, computing device 106 may be configured to first perform a rough alignment of the thermographic image data to the master image data, e.g., by aligning the thermographic image data to the gross geometry of the master image data. After the rough aligning of the thermographic image data to the master image data, computing device 116 may be configured to perform another morphing manipulation to align the thermographic image data more closely to the geometry of the master image data. For example, computing device 116 may utilize image recognition techniques to recognize similar features in the thermographic image data and the master image data (e.g., features representing smaller geometric features, such as exit orifices, internal geometric features such as pedestals, or features of internal passages 118) and morph the thermographic image data to substantially align the similar features. As another example, computing device 116 may utilize sets of coordinate associated with similar features of tested component 102 and the fabricated gold standard or theoretical component and morph the thermographic image data based on a different between positions of corresponding sets of coordinates.

In some examples, computing device 116 may be configured to morph the thermographic image data while substantially preserving (e.g., preserving or nearly preserving) the thermal response information (e.g., intensity and/or wavelength) contained in the thermographic image data. Because the thermal response information is what will be compared by computing device 116 to detect any discrepancies between the master component and the tested component 102, preserving the information during the morphing of the thermographic image data may facilitate more accurate comparisons.

Once computing device 116 has morphed the thermographic image data to substantially align the thermographic image data with the master image data, computing device 116 may compare the thermal response information from the thermographic image data to the thermal response information from the master image data. In some examples, computing device 116 may compare the thermal response information on per-pixel basis. In other examples, computing device 116 may group adjacent pixels with similar thermal response information into a set and determine representative thermal response data for each set (e.g., each set of both the thermographic image data and the master image data). Computing device 116 then may compare the thermal response information on a per-set basis.

In some examples, the thermal response data for each pixel or each set may include a single value representative of the thermal response of the location corresponding to the pixel or set over a duration of time, as described above. In other examples, the thermal response data may include a series of data representative of the sensed intensity and/or wavelength as a function of time throughout the duration of time. In either case, computing device 116 may compare the thermal response data from the thermographic image data and the thermal response data from the master image data to identify any discrepancies between the thermal data.

In some examples, computing device 116 may compare the identified discrepancies to a threshold to determine whether the discrepancies indicate a potential deficiency in tested component 102. Deficiencies may include defects, damage, blockage, holes, inclusions, wear, or the like. In some examples, a single threshold may be used for all the comparisons, e.g., for data representative of all locations of tested component 102. In other examples, computing device 116 may adaptively determine the threshold for a respective comparison based on one or more parameters. The parameters may include, for example, an amount the thermographic image data for the location was morphed to substantially align with the master image data. For example, more extensive morphing may indicate a greater likelihood that tested component 102 includes a deficiency at the location that was morphed, so computing device 116 may set the threshold for identifying a discrepancy as a potential deficiency to a lower value. The parameters additionally or alternatively relate to geometry of the component, such as wall thickness at the location or material composition of the component at the location, or may relate to testing conditions, such as the temperature of the fluid flow through internal passages 118 or ambient temperature within enclosure 104.

Computing device 116 may be configured to identify any discrepancies greater than the threshold value for each respective comparison as potential deficiencies in tested component 102. The potential deficiencies may include, for example, geometric defects (e.g., an exit orifice was formed in a position different than the design position), structural defects (e.g., cracks, delamination of a coating, disbands, or the like) in tested component 102, damage to tested component 102, a material defect (e.g., an inclusion or hole), wear, or debris within internal passages 118. In some examples, computing device 116 may be configured to both identify the presence of potential deficiencies and the type of the respective potential deficiencies. In other examples, computing device 116 may be configured to identify the presence of potential deficiencies, but not identify the type of the respective potential deficiencies.

In some examples, computing device 116 may be configured to generate a false color or a grayscale representation of the thermographic image data substantially aligned to the three-dimensional master data, with any potential deficiencies represented in the false color or grayscale representation. For example, computing device 116 may be configured to assign a particular color or grayscale intensity to potential deficiencies. The color or grayscale intensity may correlate to the difference between the discrepancy and the threshold value used to make the comparison for the respective location, which may allow a user to perceive the magnitude of the discrepancy based on the color or grayscale intensity. Computing device 116 may output the false color or grayscale representation for display at a display device.

In some examples, computing device 116 may be configured to evaluate tested component 102 based on the identified potential deficiencies. For example, computing device 116 may count the number of identified potential deficiencies and compare the number to a threshold number of deficiencies or multiple thresholds of numbers of deficiencies. For example, a first threshold number of deficiencies may be defined that separates acceptable components from marginal components and a second threshold number of deficiencies may be defined that separates marginal components from unacceptable components. Computing device 116 may be configured to compare the identified potential deficiencies to the threshold or thresholds and categorize tested component 102 based on the comparison. In some examples, rather than performing the counting and comparison for the entire tested component 102, computing device 116 may be configured to divide tested component 102 into a plurality of logical portions and perform the counting and comparison on a per-portion basis. Computing device 116 may be configured to categorize the individual logical portions based on the counting and comparison. In some examples, computing device 116 may be configured to evaluate a size of a potential deficiency or a severity of a potential deficiency in addition to evaluating a number of potential deficiencies per logical portion or per tested component 102.

Figure 6:
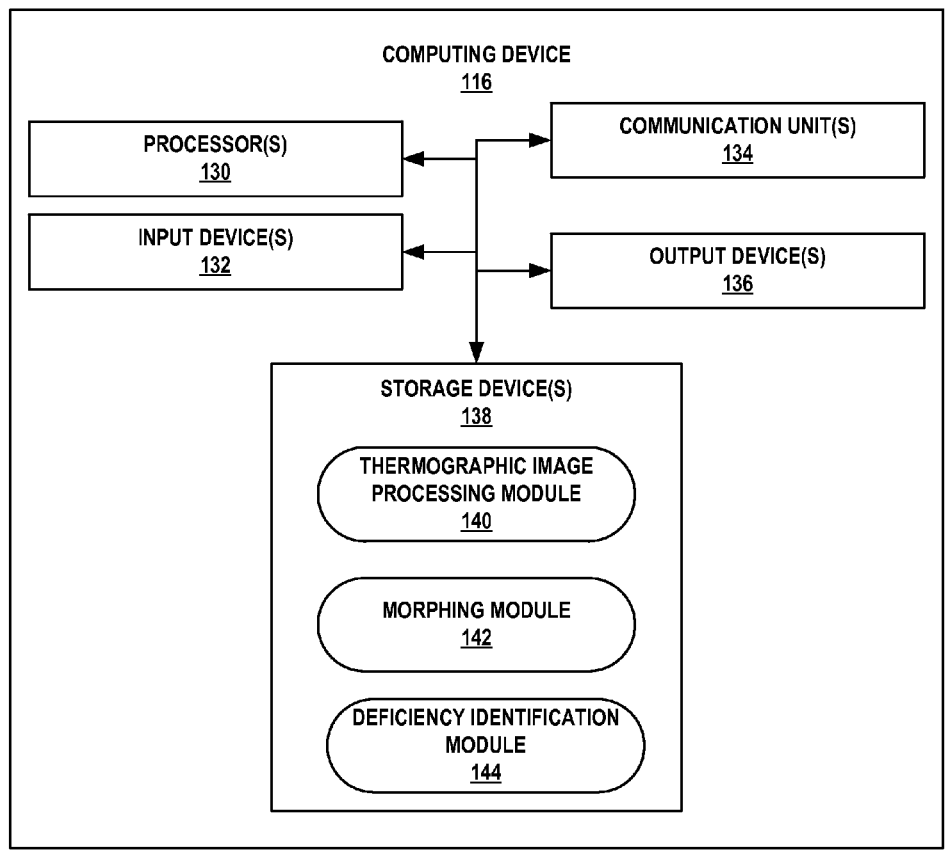
FIG. 6 is a conceptual block diagram illustrating an example of a computing device.

FIG. 6 is a conceptual block diagram illustrating an example of computing device 116 illustrated in FIG. 5. In the example illustrated in FIG. 6, computing device 116 includes one or more processors 130, one or more input devices 132, one or more communication units 134, one or more output devices 136, and one or more storage devices 138. In some examples, one or more storage devices 138 stores thermographic image module 140, image morphing module 142, and deficiency identification module 144. In other examples, computing device 116 may include additional components or fewer components than those illustrated in FIG. 6.

One or more processors 130 are configured to implement functionality and/or process instructions for execution within computing device 116. For example, processors 130 may be capable of processing instructions stored by storage device 138. Examples of one or more processors 130 may include any one or more of a microprocessor, a controller, a DSP, an ASIC, a FPGA, or equivalent discrete or integrated logic circuitry.

One or more storage devices 138 may be configured to store information within computing device 116 during operation. Storage devices 138, in some examples, include a computer-readable storage medium or computer-readable storage device. In some examples, storage devices 138 include a temporary memory, meaning that a primary purpose of storage device 138 is not long-term storage. Storage devices 138, in some examples, include a volatile memory, meaning that storage device 138 does not maintain stored contents when power is not provided to storage device 138. In some examples, storage devices 138 may further include one or more storage device 138 configured for longer-term storage of information. In some examples, storage devices 138 include non-volatile storage elements.

Computing device 116 further includes one or more communication units 134. Computing device 116 may utilize communication units 134 to communicate with external devices (e.g., stage 106, thermal camera 108, heat source 110, and/or valves 114) via one or more networks, such as one or more wired or wireless networks. Computing device 16 also includes one or more input devices 132. Input devices 132, in some examples, are configured to receive input from a user through tactile, audio, or video sources. Examples of input devices 132 include a mouse, a keyboard, a voice responsive system, video camera, microphone, touchscreen, or any other type of device for detecting a command from a user.

Computing device 116 may further include one or more output devices 136. Output devices 136, in some examples, are configured to provide output to a user using audio or video media. For example, output devices 136 may include a display, a sound card, a video graphics adapter card, or any other type of device for converting a signal into an appropriate form understandable to humans or machines.

Computing device 136 also may include thermographic image processing module 140, image morphing module 142, and deficiency identification module 144. Thermographic image processing module 140, image morphing module 142, and deficiency identification module 144 may be implemented in various ways. For example, thermographic image processing module 140, image morphing module 142, and/or deficiency identification module 144 may be implemented as an application executed by one or more processors 40. In other examples, thermographic image processing module 140, image morphing module 142, and/or deficiency identification module 144 may be implemented as part of a hardware unit of computing device 20 or as part of an operating system provided by computing device 20. Functions performed by thermographic image processing module 140, image morphing module 142, and deficiency identification module 144 are explained below with reference to the example flow diagrams illustrated in FIG. 7.

Computing device 116 may include additional components that, for clarity, are not shown in FIG. 6. For example, computing device 116 may include a power supply to provide power to the components of computing device 116. Similarly, the components of computing device 116 shown in FIG. 6 may not be necessary in every example of computing device 116.

Figure 7:
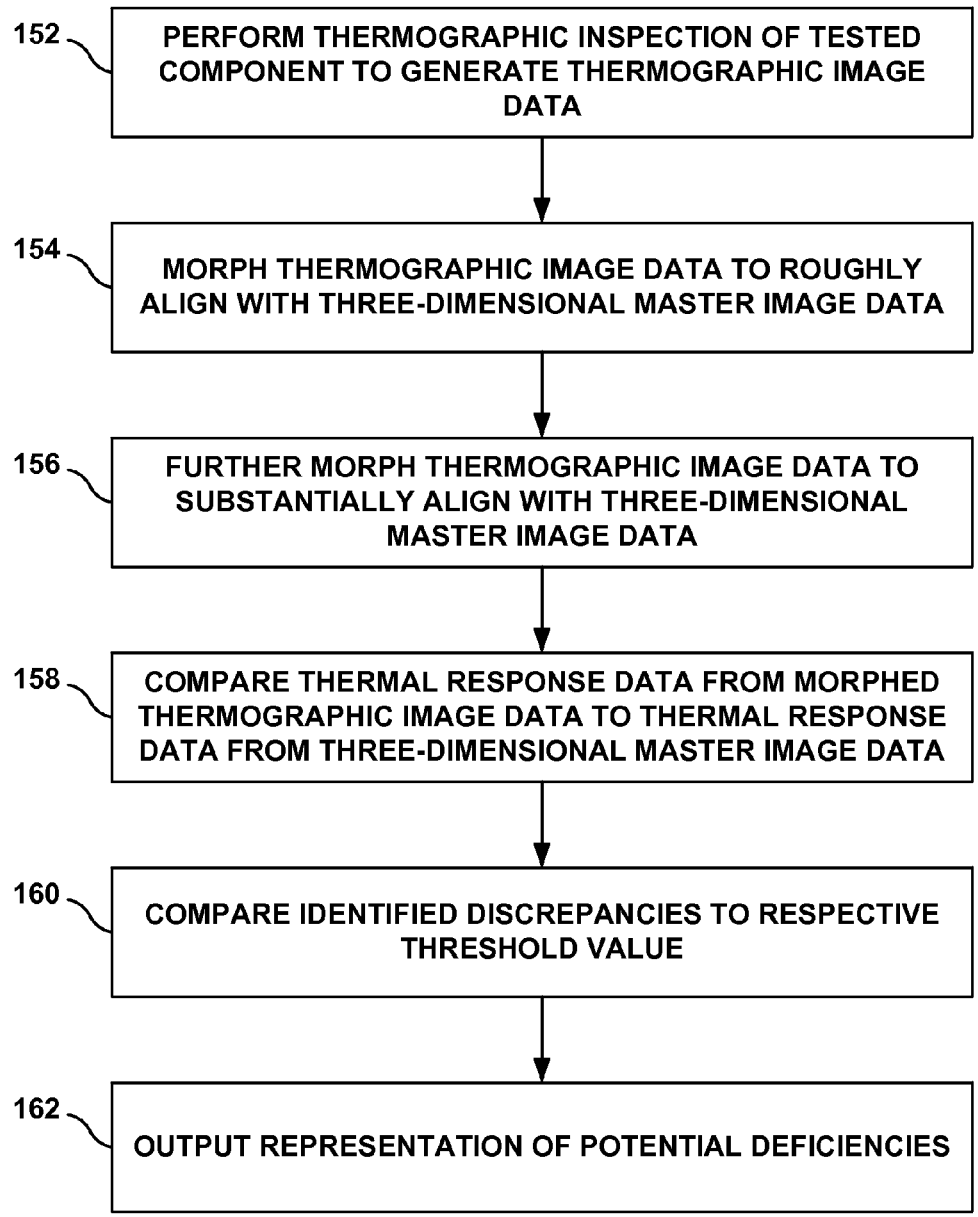
FIG. 7 is a flow diagram illustrating an example technique for identifying discrepancies between two-dimensional thermographic data and master image data.

In accordance with some examples of the disclosure, computing device 116 (e.g., image morphing module 142) may be configured to morph thermographic image data to substantially align with master image data. In some examples, deficiency identification module 114 may be configured to compare the morphed thermographic image data to the master image data to identify discrepancies between the morphed thermographic image data and the master image data. In some examples, deficiency identification module 144 may be configured to identify potential deficiencies in tested component 102 based on the discrepancies between the morphed thermographic image data and the master image data. FIG. 7 is a flow diagram illustrating an example technique for associating flow values measured using a fabricated gold standard component with flowing thermographic image data. Although the technique of FIG. 7 will be described with respect to system 100 of FIG. 4 and computing device 116 of FIG. 5, in other examples, the technique of FIG. 7 may be performed using a different system. Additionally, system 100 and computing device 116 may perform other techniques to morph thermographic image data to substantially align with master image data and identify potential deficiencies based on a comparison of the morphed thermographic image data and the master image data.

The technique of FIG. 7 includes performing thermographic inspection of tested component 102 to generate thermographic image data (152). As described above either or both of flowing thermography or flash thermography may be used to generate the thermographic image data. In flash thermography, computing device 116 (e.g., one or more processors 130) control heat source 110 to apply heat (e.g., a pulse of infrared radiation) to the outer surface of tested component 102. Thermal camera 108 captures image data representative of the surface temperature of tested component 102 over time, which provides the thermal response of tested component 102 to the heat provided by heat source 110. Computing device 116 (e.g., thermographic image processing module 140) then received the thermographic image data from thermal camera 108. In flowing thermography, computing device 116 (e.g., one or more processors 130) controls flow valve to open a predetermined amount for a predetermined time to allow a predetermined pulse of fluid to flow from fluid source 112 to plenum 120 and through internal passages 118 of tested component 102. Thermal camera 108 captures image data representative of the surface temperature of tested component 102 over time in response to the pulse of fluid. Computing device 116 (e.g., thermographic image processing module 140) then received the thermographic image data from thermal camera 108. As described above, the thermographic image data may include data for respective pixels from a sensor of thermal camera 108. The data for each pixel may include intensity and/or wavelength over time, representative of a temperature of the location from which the pixel is sensing thermal radiation (e.g., a location on tested component 102).

In some examples, thermographic image processing module 140 may process the thermographic image data received from thermal camera 108. For example, thermographic image processing module 140 may be configured to determine a single value representative of the thermal response of a location of tested component 102 (e.g., represented by a pixel or a set of adjacent pixels) over a duration of time. For example, the duration may be from the initial change in temperature of the location from the equilibrium temperature until the location returns to the equilibrium temperature. The single value may incorporate at least one attribute of the thermal response of the location, including, for example, maximum temperature, minimum temperature, rate of temperature change, time to return to equilibrium temperature, or the like.

In some examples, thermographic image processing module 140 may be configured to combine thermographic image data from a plurality of thermography tests. For example, each thermographic test may result in thermographic image data for a portion of tested component 102 (e.g., a portion at which thermal camera 108 is directed). A plurality of thermographic tests may be utilized to collect thermographic image data for the entire surface area of tested component 102. thermographic image processing module 140 may be configured to combine a plurality of sets of thermographic image data into a single set of thermographic image data representative of the thermal response of a predetermined portion of component 102 (e.g., substantially all exposed surfaces of tested component 102). For example, each set of thermographic image data may be associated with a set of coordinates representative of the orientation of tested component 102 relative to thermal camera 108. Thermographic image processing module 140 may be configured to combine the plurality of sets of thermographic image data based on the coordinates of the respective sets of thermographic image data. In other examples, thermographic image processing module 140 may be configured to perform one or more image recognition techniques to recognize similar features (e.g., representative of the same exit orifice) in two sets of thermographic image data and combine the two sets of thermographic image data based on the similar features.

The technique of FIG. 7 also includes morphing the thermographic image data to roughly align with master image data (154). In some examples, computing device 116 includes an image morphing module 142. Image morphing module 142 may be configured to receive the thermographic image data from thermographic image processing module 140. Image morphing module 142 also may be configured to receive master image data.

The master image data may be representative of three-dimensional geometry and thermal response of a theoretical component, a fabricated gold standard component, or an average geometry and thermal response of a plurality of tested components 102, as described above. In some examples, the three-dimensional geometry of the master image data may be representative of the geometry that tested component 102 was designed to possess. However, the actual geometry of tested component 102 may depart from the geometry of the master image data due to manufacturing tolerances, damage to component 102, wear of component 102 during use, defects in tested component 102, or the like.

Image morphing module 142 may be configured to morph (e.g., translate, rotate, scale, and/or stretch) the thermographic image data to roughly align with the master image data (154). As used herein, "roughly align" means that the morphed two-dimensional thermographic image data generally aligns to the master image data based on general or rough geometry of the master image data, while relatively more precise geometrical features may remain not substantially aligned.

For example, image morphing module 142 may be configured to overlay thermographic image data on the geometry defined by the master image data, e.g., based on the approximate surface geometry defined by the master image data and the approximate surface geometry represented in the thermographic image data. As another example, image morphing module 142 may be configured to roughly align the thermographic image data and the master image data based on sets of coordinates representative of the orientation of tested component 102 relative to thermal camera 108 and sets of coordinates representative of the orientation (real or theoretical) of the three-dimensional image data relative to thermal camera 108. As described above, in some examples, the thermographic image data may include sets of coordinates associated with respective features of the image data, such that individual geometric features of component 102 are associated with sets of coordinates (e.g., each exit orifice may be associated with a respective set of coordinates). In some examples, tested component 102 may include one or more features that is included in tested component 102 to facilitate identification of the relative orientation of tested component 102 to thermal camera 108. In other examples, image morphing module 142 may utilize geometric features such as exit orifices (e.g., film cooling holes, a feature at a perimeter of tested component 102) to identify the orientation of tested component relative to thermal camera 108. Alternatively or additionally, the location of tested component relative to stage 106 may be substantially fixed (e.g., fixed or nearly fixed) and substantially consistent (e.g., consistent or nearly consistent), and the thermographic image data may be associated with coordinates representing the position of stage 106 relative to thermal camera 108.

Similarly, portions of the master image data may be associated with respective sets of coordinates representative of the real or theoretical orientation of the master image data relative to thermal camera 108, such that individual geometric features of the fabricated gold standard component or theoretical component are associated with sets of coordinates (e.g., each exit orifice may be associated with a respective set of coordinates). Alternatively or additionally, when the master image data is based on a fabricated gold standard component or an average of results from a plurality of tested components 102, the location of the fabricated gold standard component or the average geometry of the plurality of tested components 102 relative to stage 106 may be substantially fixed (e.g., fixed or nearly fixed) and substantially consistent (e.g., consistent or nearly consistent), and the master image data may be associated with coordinates representing the position of stage 106 relative to thermal camera 108.

Regardless of how the sets of coordinates for the thermographic image data and the master image data are defined, image morphing module 142 may be configured to utilize the sets of coordinates for the thermographic image data and the sets of coordinates associated with the master image data to perform a first morphing operation (e.g., including translating, rotating, scaling, and/or stretching the thermographic image data) and roughly align the thermographic image data to the master image data (154).

Image morphing module 142 may be configured to morph the thermographic image data while substantially preserving (e.g., preserving or nearly preserving) the thermal response information (e.g., intensity and/or wavelength) contained in the thermographic image data. In other words, image morphing module 142 may morph the geometric information contained in thermographic image data (e.g., by applying one or more offsets to a value or set representative of pixel location to shift the relative pixel location while substantially preserving the thermal response information associated with the pixel. Because the thermal response information is what will be compared by computing device 116 to detect any discrepancies between the master component and the tested component 102, preserving the thermal response information during the morphing of the thermographic image data may facilitate more accurate comparisons between the thermographic image data and the master image data.

Once the image morphing module 142 has roughly aligned the thermographic image data to the master image data (154), image morphing module 142 may further morph the thermographic image data to substantially align with the master image data (156). For example, image morphing module 142 may utilize image recognition techniques to recognize similar features in the thermographic image data and the master image data (e.g., features representing smaller geometric features, such as exit orifices, internal geometric features such as pedestals, or features of internal passages 118) and morph the thermographic image data to substantially align the similar features. In some examples, during the further morphing step, image morphing module 142 may use image recognition techniques to recognize more precise (e.g., smaller) features in the thermographic image data and/or the master image data and may utilize the more precise features to achieve better alignment between the thermographic image data and the master image data. Examples of more precise features that image morphing module 142 may recognize include cooling circuit geometry (e.g., geometry of internal passages 118), internal pedestals (e.g., pedestals of a gas turbine engine blade to which a sheet that defines the external surface of the gas turbine engine blade is attached), exit orifices (e.g., film cooling holes of a gas turbine engine blade), or the like. Like when image morphing module 142 is morphing the thermographic image data to roughly align with the master image data, image morphing module 142 may morph the geometric component of the thermographic image data while substantially preserving the thermal response data for the thermographic image data.

In some examples, image morphing module 142 may iteratively morph (e.g., translate, rotate, stretch, and/or scale) the thermographic image data until the thermographic image data substantially aligns with (e.g., aligns with or nearly aligns with) the master image data. In some examples, image morphing module 142 may determine when the thermographic image data is substantially aligned with the master image data based on a determine of whether at least one geometric feature (e.g., a plurality of features) of the thermographic image data is substantially aligned with the corresponding at least one geometric feature of the master image data. For example, image morphing module 142 may determine, for each geometric feature of the plurality of geometric features, whether the thermographic image data substantially aligns with the master image data. Image morphing module 142 may then determine whether the number of features that substantially align (e.g., align or nearly align) are greater than a threshold number of features. Responsive to determining that the number of features that substantially align is greater than the threshold number of features, image morphing module 142 may determine that the thermographic image data is substantially aligned with the master image data. However, responsive to determining that the number of features that substantially align is less than the threshold number of features, image morphing module 142 may determine that the thermographic image data is not substantially aligned with the master image data, and may perform additional image morphing steps.

Once image morphing module 142 determines that the thermographic image data is substantially aligned with the master image data, deficiency identification module 144 may compare the thermal response data from the thermographic image data to thermal response data from the master image data (158). In some examples, deficiency identification module 144 may compare the thermal response information on per-pixel basis. That is, for each pixel of the thermographic image data, deficiency identification module 144 may compare the thermal response data from the thermographic image data to the thermal response data for the corresponding pixel of the master image data.

In other examples, for both the thermographic image data and the master image data, deficiency identification module 144 may group adjacent pixels with similar thermal response information into a set and determine representative thermal response data for each set. Computing device 116 then may compare the thermal response information on a per-set basis. That is, for each set of the thermographic image data, deficiency identification module 144 may compare the thermal response data from the thermographic image data to the thermal response data for the corresponding set of the master image data.

As described above, in some examples, the thermal response data for each pixel or each set may include a single value representative of the thermal response of the location corresponding to the pixel or set over a duration of time. In other examples, the thermal response data may include a series of data representative of the sensed intensity and/or wavelength as a function of time throughout the duration of time. In either case, deficiency identification module 144 may compare the thermal response data from the thermographic image data and the thermal response data from the master image data to identify any discrepancies between the thermal response data from the thermographic image data and the thermal response data from the master image data.

Deficiency identification module 144 then may compare each identified discrepancy to a respective threshold value to determine whether the respective identified discrepancy indicates a potential deficiency in tested component 102 (160). In some examples, the threshold value for each identified discrepancy may be the same. In other examples, at least one threshold values may be different than another threshold value. The threshold value(s) may be determined based at least in part on one or more parameters associated with the thermographic image data and/or the master image data. Example parameters may include an amount the thermographic image data for the location corresponding to the location of the respective potential deficiency was morphed; a parameter relating to the geometry of tested component 102 at the location of the respective potential deficiency, such as wall thickness; a material property of tested component 102 at the location; and/or testing conditions, such as the temperature of the fluid flow through internal passages 118 or ambient temperature within enclosure 104.

For example, more extensive morphing of the thermographic image data corresponding to the identified discrepancy may indicate a greater likelihood that tested component 102 includes a deficiency at the location that was morphed, so deficiency identification module 144 may set the threshold for identifying a discrepancy as a potential deficiency to a lower value. Conversely, less morphing of the thermographic image data corresponding to the identified discrepancy may indicate a lower likelihood that tested component 102 includes a deficiency at the location that was morphed, so deficiency identification module 144 may set the threshold for identifying a discrepancy as a potential deficiency to a higher value.

Deficiency identification module 144 may compare each identified discrepancy to the respective threshold value to determine whether the respective identified discrepancy indicates a potential deficiency in tested component 102 (160). Deficiency identification module 144 may be configured to identify any discrepancies greater than the respective threshold value as potential deficiencies within tested component 102. The potential deficiencies may include, for example, geometric defects (e.g., an exit orifice was formed in a position different than the design position), structural defects (e.g., cracks, delamination of a coating, disbands, or the like) in tested component 102, damage to tested component 102, a material defect (e.g., an inclusion or hole), wear, or debris within internal passages 118. Each of these deficiencies may affect fluid flow within internal passages 118 and/or heat transfer within tested component 102.

Deficiency identification module 144 then may output a representation of the identified potential deficiencies (162). For example, deficiency identification module 144 may be configured to generate a false color or a grayscale representation of the thermographic image data substantially aligned to the three-dimensional master data, with any identified potential deficiencies represented in the false color or grayscale representation. For example, deficiency identification module 144 may be configured to assign a particular color or grayscale intensity to potential deficiencies. The color or grayscale intensity may correlate to the difference between the discrepancy and the threshold value used to make the comparison for the respective location, which may allow a user to perceive the magnitude of the discrepancy based on the color or grayscale intensity. Deficiency identification module 144 may output the false color or grayscale representation for display at a display device included in or coupled to computing device 116 (e.g., one of output devices 136).

As another example, deficiency identification module 144 may be configured to count the number of identified potential deficiencies and compare the number to at least one threshold number of deficiencies. For example, deficiency identification module 144 may compare the number of identified potential deficiencies to a threshold number of deficiencies and determine whether tested component 102 is acceptable or not acceptable based on the comparison. Responsive to determining that the number of identified potential deficiencies is greater than the threshold number of deficiencies, deficiency identification module 144 may determine that tested component 102 is unacceptable. Responsive to determining that the number of identified potential deficiencies is less than the threshold number of deficiencies, deficiency identification module 144 may determine that the tested component 102 is acceptable.

As another example, deficiency identification module 144 may compare the number of identified potential deficiencies to a first threshold number of deficiencies to determine whether the tested component 102 is acceptable. Responsive to determining that the number of identified potential deficiencies is less than the first threshold number of deficiencies, deficiency identification module 144 may determine that the tested component 102 is acceptable. Responsive to determining that the number of identified potential deficiencies is less than the threshold number of deficiencies, deficiency identification module 144 may compare the number of identified potential deficiencies to a second threshold number of deficiencies. The second threshold number of deficiencies may be selected to discriminate between marginal components and unacceptable components. Responsive to determining that the number of identified potential deficiencies is greater than the second threshold number of deficiencies, deficiency identification module 144 may determine that tested component 102 is unacceptable. Responsive to determining that the number of identified potential deficiencies is less than the second threshold number of deficiencies, deficiency identification module 144 may determine that the tested component 102 is marginal. In some examples, deficiency identification module 144 may be configured to output an indication of the categorization of tested component 102, and, in some examples, further information regarding the number and/or location of the identified potential deficiencies.

In some examples, rather than performing the counting and comparisons on a per-component basis, deficiency identification module 144 may be configured to logically divide tested component 102 (e.g., the thermographic image data representative of tested component 102) into a plurality of portions. Deficiency identification module 144 then may count identified potential deficiencies on a per-portion basis, and, for each portion, compare the number of identified potential deficiencies to at least one threshold number of deficiencies. In some examples, deficiency identification module 144 may be configured to output an indication of the categorization of each portion of tested component 102, and, in some examples, further information regarding the number and/or location of the identified potential deficiencies in each portion of tested component 102.

In some examples, computing device 116 may be configured to evaluate a size of a potential deficiency or a severity of a potential deficiency (e.g., based at least in part on the magnitude of the discrepancy between the master image data and the thermographic image data) in addition to evaluating a number of potential deficiencies per logical portion or per tested component 102.

In this way, morphing the thermographic image data to substantially align with master image data and comparing the morphed thermographic image data to the master image data may facilitate identification potential deficiencies in tested component 102. In some examples, the morphing procedure and the comparison between the thermographic image data and the master image data may be automated (e.g., carried out by computing device 116 automatically with little or no under intervention after initiating the technique). In some examples, computing device 116 may output a representation of the identified potential deficiencies, which a trained technician may view and use to determine whether tested component 102 is acceptable or unacceptable. In some examples, computing device 116 may automatically make a determination of whether tested component is acceptable or unacceptable (and, optionally, marginal) based on the number and/or severity of the identified potential deficiencies.

Figure 8:
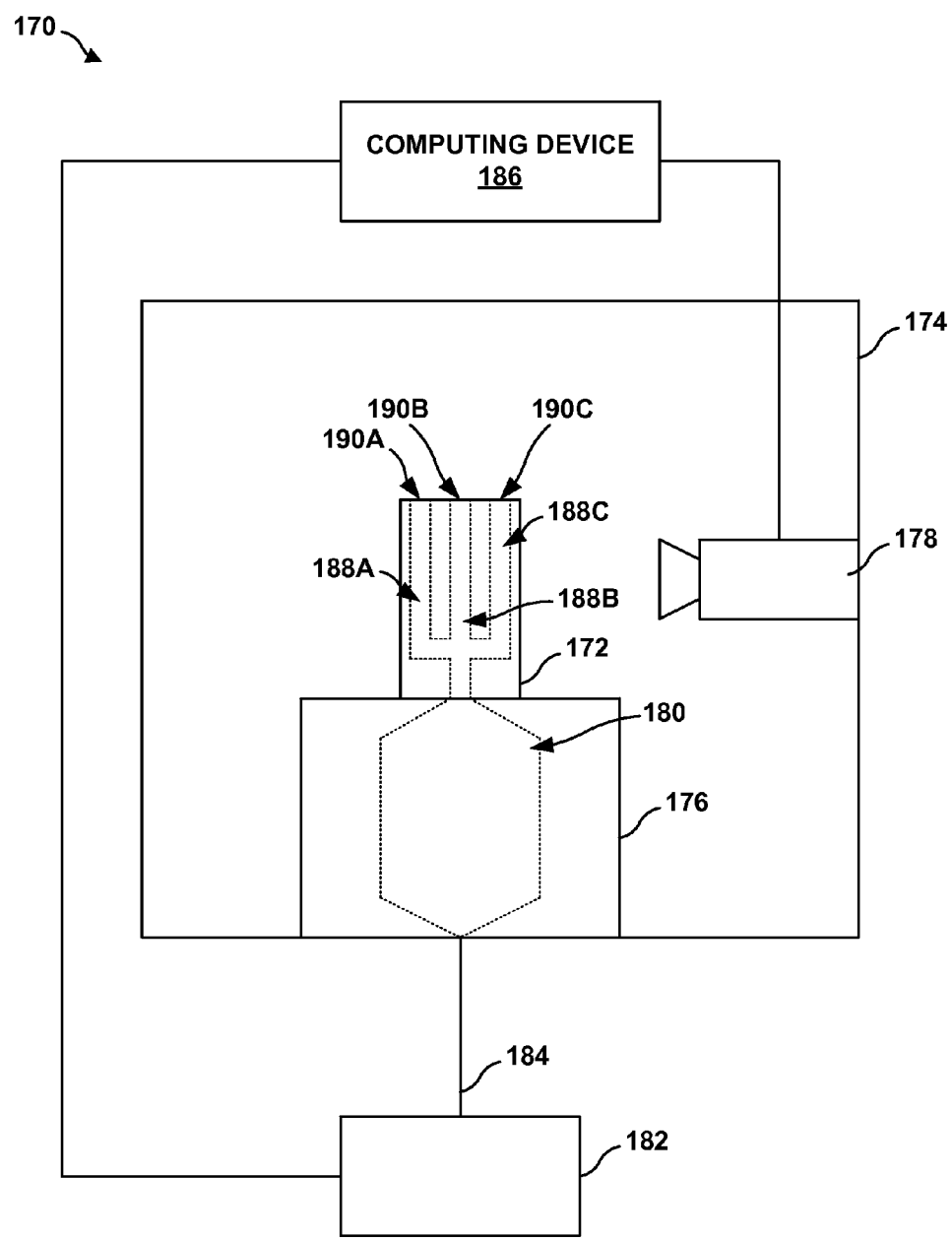
FIG. 8 is a conceptual block diagram illustrating an example system for performing both cleaning of internal passages of a component using dry ice and flowing thermography inspection of the component using dry ice.

In some examples, as described above, a single inspection station may include components that allow both cleaning of internal passages of the component using dry ice and flowing thermography inspection of the component. FIG. 8 is a conceptual block diagram illustrating an example system 170 for performing both cleaning of internal passages of a component 172 using dry ice and flowing thermography inspection of the component 172. Performing the cleaning using dry ice and flowing thermography at a single inspection station may be more time and space efficient than utilizing two separate stations for the cleaning and the flowing thermography testing. Further, in examples in which dry ice is used to flowing thermography, cleaning and performing flowing thermography substantially simultaneously may be more time efficient that performing the procedures sequentially.

System 170 may be similar to or substantially the same (e.g., the same or nearly the same) as system 10 described with reference to FIG. 1. For example, like system 10, system 100 includes an enclosure 174 defining an inspection station, a stage 176 defining a plenum 180, a thermal camera 178, a valve 184, a computing device 186, and a flow line 184. These components may be similar to or substantially the same as the corresponding components described with respect to FIG. 1. For example, stage 176 may be movable (e.g., translatable and/or rotatable) in at least one dimension and/or thermal camera 178 may be movable (e.g., translatable and/or rotatable) in at least one dimension to position tested component 172 with respect to thermal camera 178.

Although not illustrated in FIG. 8, system 170 also may include a heat source (e.g., heat source 110 illustrated in FIG. 5). By including a heat source, system 170 also may be configured to perform flash thermography on tested component 172. In this way, in some examples, system 170 may be configured to perform cleaning using dry ice, flowing thermography testing, and flash thermography on tested component 172 at a single inspection station.

Unlike system 10 of FIG. 1, system 170 includes a dry ice source 182. Dry ice source 182 may be fluidically coupled to plenum 180 by flow line 184. Computing device 186 may be configured to control dry ice source 182 to control introduction of dry ice into plenum 180, and, ultimately, internal passages 188 of tested component 172.

FIG. 8 also illustrates exit orifices 190A, 190B, and 190C (collectively, "exit orifices 190") defined in tested component 172. First exit orifice 190A is fluidically coupled to first internal passage 188A and defines the exit point from fluid flowing through internal passage 188A. Similarly, second exit orifice 190B is fluidically coupled to second internal passage 188B, and third exit orifice 190C is fluidically coupled to second internal passage 188C. In some examples, internal passages 188 may include internal cooling channels, and exit orifices 190 may include film cooling holes.

Figure 9:
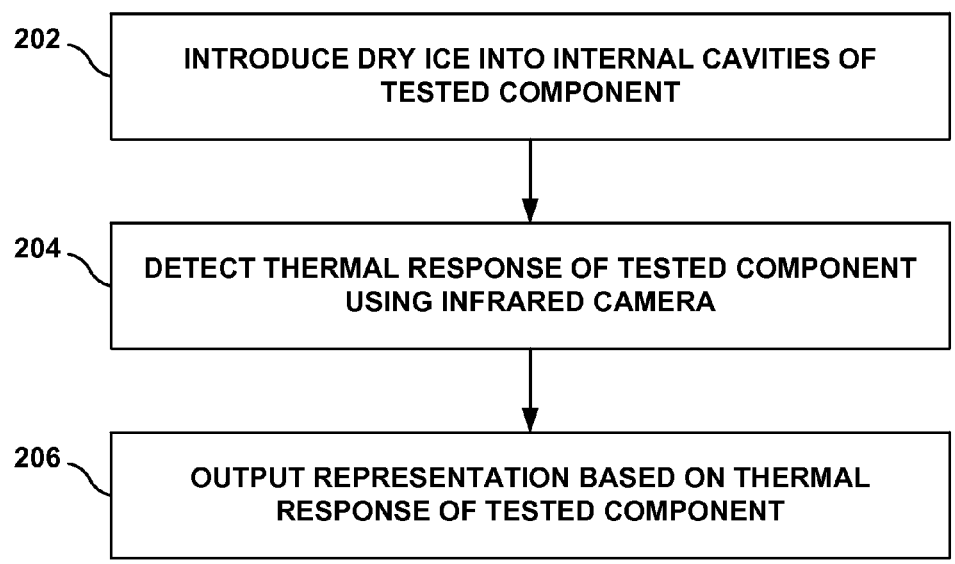
FIG. 9 is a flow diagram illustrating an example technique for cleaning a tested component using dry ice and performing flowing thermography on the tested component using dry ice.

FIG. 9 is a flow diagram illustrating an example technique that may be implemented by system 170 (e.g., under control of computing device 186) to clean tested component 172 and perform flowing thermography on tested component 172 using dry ice. Although the technique of FIG. 9 will be described with respect to system 170 of FIG. 8, in other examples, the technique of FIG. 9 may be performed using a different system. Additionally, system 170 may perform other techniques to clean tested component 172 and perform flowing thermography on tested component 172.

The technique illustrated in FIG. 9 includes introducing dry ice into internal passages 188 of tested component 172 (202). Computing device 186 may be configured to control dry ice source 182 to control introduction of dry ice into plenum 180, and, ultimately, internal passages 188 of tested component 172.

The dry ice may be in solid form, such as powder, pellets, shavings, or the like, and may impact any debris within internal passages 188. The debris may be present within internal passages 188 due to ingestion of dust, dirt, or other particulates during use of tested component 172, e.g., as a blade of a gas turbine engine. Alternatively or additionally, the debris may have been formed during manufacture of tested component 172, e.g., may be a portion of a casting used to define internal passages 188 during formation of tested component 172. The introduction of dry ice into internal passages 188 may cause the debris to release from the walls of the internal passages and/or shatter into smaller pieces and be carried out of internal passages 188 through exit orifices 190 with the dry ice. In some examples, at least a portion of the dry ice may sublimate to vapor within internal passages 188. Exiting of gaseous dry ice from a respective one of exit orifices 190 may be used to confirm clear flow within the respective exit orifice 190. In this way, the dry ice may be used to clean internal passages 188 of debris.

The introduction of dry ice into internal passages 188 may produce a transient temperature change of tested component 172 from an equilibrium temperature (e.g., the temperature of the surrounding atmosphere). The technique of FIG. 9 also includes detecting the thermal response of tested component 172 using thermal camera 178 (204). As the dry ice is introduced into and travels through internal passages 188 and out through the corresponding exit orifices 190, thermal camera 178 may capture data representative of the temperature of the surface of tested component 172, with each individual sensor (e.g., corresponding to a pixel) of thermal camera 178 capturing data representative of the temperature of particular location of tested component 172 over time. The thermographic image data may include, for example, the wavelength and/or intensity of radiation detected by each individual sensor as a function of time. Computing device 186 may be configured to receive the thermographic image data from thermal camera 178.

The technique of FIG. 9 further includes outputting a representation based on the thermal response of tested component 172 (206). In some examples, computing device 186 may process the thermographic image data received from thermal camera 178. For example, computing device 186 may be configured to determine a single value representative of the thermal response of a location of tested component 172 (e.g., represented by a pixel or a set of adjacent pixels) over a duration of time. For example, the duration may be from the initial change in temperature of the location from the equilibrium temperature until the location returns to the equilibrium temperature. The single value may incorporate at least one attribute of the thermal response of the location, including, for example, maximum temperature, minimum temperature, rate of temperature change, time to return to equilibrium temperature, or the like.

In some examples, computing device 186 may be configured to combine thermographic image data from a plurality of thermography tests. For example, each thermographic test may result in thermographic image data for a portion of tested component 172 (e.g., a portion at which thermal camera 178 is directed). A plurality of thermographic tests may be utilized to collect thermographic image data for the entire surface area of tested component 172. Computing device 186 may be configured to combine a plurality of sets of thermographic image data into a single set of thermographic image data representative of the thermal response of a predetermined portion of tested component 172 (e.g., substantially all exposed surfaces of tested component 172). For example, each set of thermographic image data may be associated with a set of coordinates representative of the orientation of tested component 172 relative to thermal camera 178. Computing device 186 may be configured to combine the plurality of sets of thermographic image data based on the coordinates of the respective sets of thermographic image data. In other examples, computing device 186 may be configured to perform one or more image recognition techniques to recognize similar features (e.g., representative of the same exit orifice) in two sets of thermographic image data and combine the two sets of thermographic image data based on the similar features.

In some examples, outputting a representation based on the thermal response of tested component 172 (206) may include outputting a false color or a grayscale representation of the thermographic image data. For example, computing device 186 may be configured to associate respective single values with corresponding false color values or corresponding grayscale values. Computing device 186 may then output the false color or grayscale representation for display at a display device included in or operatively coupled to computing device 186.

As another example, computing device 186 may be configured to morph the thermographic image data to substantially align with three-dimensional master data as described above with respect to FIGS. 5-7, and computing device 186 may be configured to compare the thermographic image data to the three-dimensional master data to identify any potential deficiencies. Computing device 186 may be configured to assign a particular color or grayscale intensity to potential deficiencies. The color or grayscale intensity may correlate to the difference between the discrepancy and the threshold value used to make the comparison for the respective location, which may allow a user to perceive the magnitude of the discrepancy based on the color or grayscale intensity. Computing device 186 may output the false color or grayscale representation for display at a display device included in or coupled to computing device 186.

As another example, computing device 186 may be configured to receive the thermographic image data and flow rate data measured by at least one flow meter during, prior to, or after the flowing thermography test, as described above with respect to FIGS. 1-4. Computing device 186 may associate flow values with the thermographic image data based on the flow rate data to generate quantitative flowing thermography image data. Computing device 186 may be configured to assign a particular color or grayscale intensity to respective flow values. Computing device 186 may output the false color or grayscale representation for display at a display device included in or coupled to computing device 186.

Figure 10:
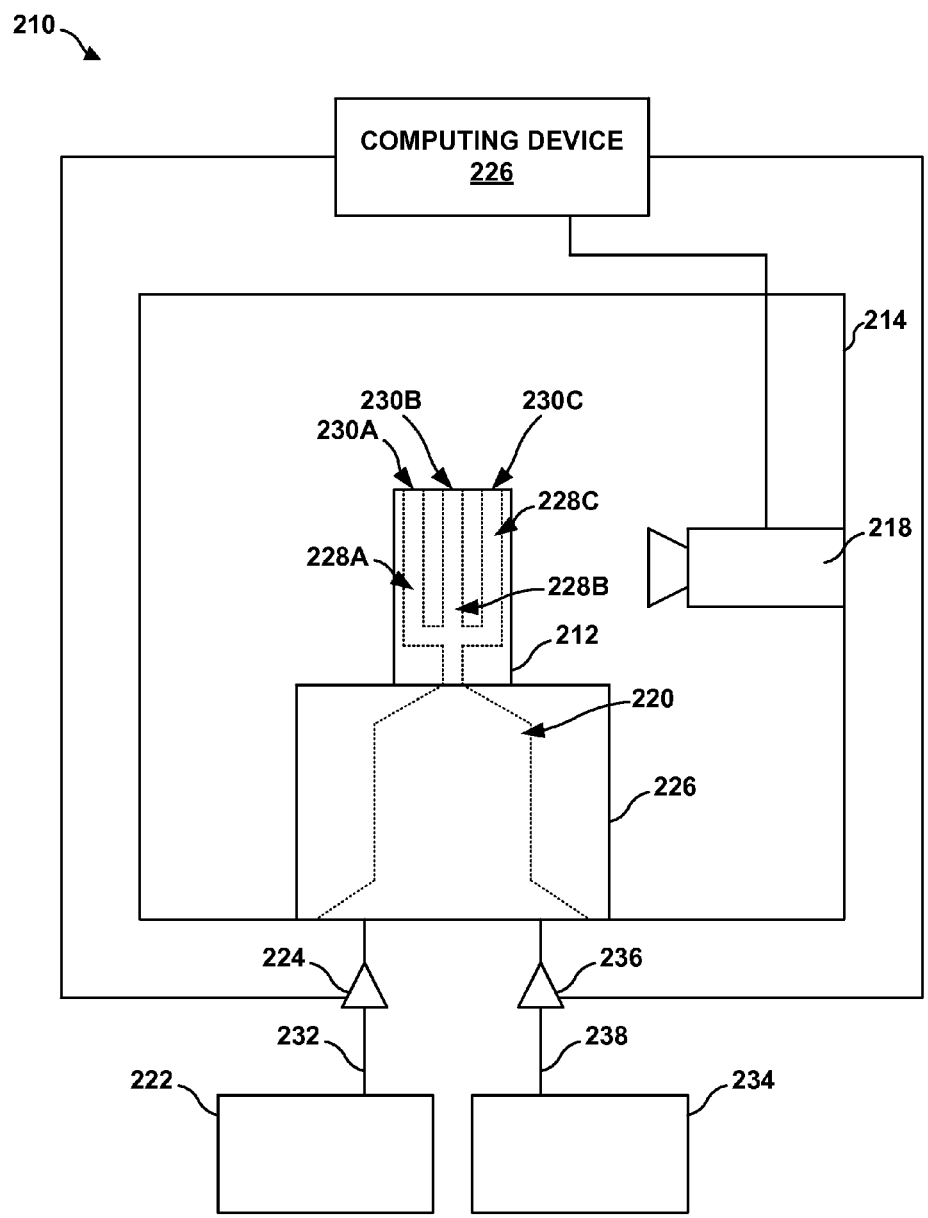
FIG. 10 is a conceptual block diagram illustrating another example system for performing both cleaning of internal passages of a component using dry ice and flowing thermography inspection of the component using a fluid.

While FIGS. 8 and 9 illustrate a system and describe a technique for substantially simultaneously (e.g., simultaneously or nearly simultaneously) cleaning component 172 and performing flowing thermography testing of component 172 using dry ice, in other examples, a system may be configured to clean a component using dry ice and then perform flowing thermography testing of the component using a fluid source. FIG. 10 is a conceptual diagram illustrating an example system 210 cleaning a tested component 212 using dry ice and performing flowing thermography on the tested component 212 using a fluid. Performing the cleaning using dry ice and flowing thermography at a single inspection station may be more time and space efficient than utilizing two separate stations for the cleaning and the flowing thermography testing.

System 210 may be similar to or substantially the same (e.g., the same or nearly the same) as system 170 described with reference to FIG. 8. For example, like system 170, system 210 includes an enclosure 214 defining an inspection station, a stage 216 defining a plenum 220, a thermal camera 218, and a computing device 186. These components may be similar to or substantially the same as the corresponding components described with respect to FIG. 8. For example, stage 216 may be movable (e.g., translatable and/or rotatable) in at least one dimension and/or thermal camera 218 may be movable (e.g., translatable and/or rotatable) in at least one dimension to position tested component 212 with respect to thermal camera 218.

Although not illustrated in FIG. 10, system 210 also may include a heat source (e.g., heat source 110 illustrated in FIG. 5). By including a heat source, system 210 also may be configured to perform flash thermography on tested component 212. In this way, in some examples, system 210 may be configured to perform cleaning using dry ice, flowing thermography testing, and flash thermography on tested component 212 at a single inspection station.

Unlike system 170 of FIG. 8, system 210 includes a dry ice source 222 and a fluid source 234. Dry ice source 222 includes a source of dry ice (e.g., solid dry ice in the form of pellets, powder, shavings, or the like). Dry ice source 222 may be fluidically coupled to plenum 220 by flow line 232. Computing device 226 may be configured to control dry ice source 222 to control introduction of dry ice into plenum 220, and, ultimately, internal passages 228 of tested component 212.

Fluid source 234 includes a source of fluid, such as compressed air, for use during flowing thermography measurement and/or flow measurements. In some examples, fluid source 234 may be configured to supply one or more liquids or other gases in addition to or in place of air. In some examples, fluid source 234 is configured to supply cooled fluid to tested component 212. In other examples, fluid source 234 may be configured to supply to component 212 a hot fluid and/or a room temperature fluid in addition to or in place of a cooled fluid. As shown in FIG. 10, fluid source 234 is fluidically coupled to plenum 220 by a fluid line 238. Valve 236 is controllable (e.g., by computing device 226) to open and close valve 236 to control a flow rate of fluid from fluid source 234 to plenum 220.

Figure 11:
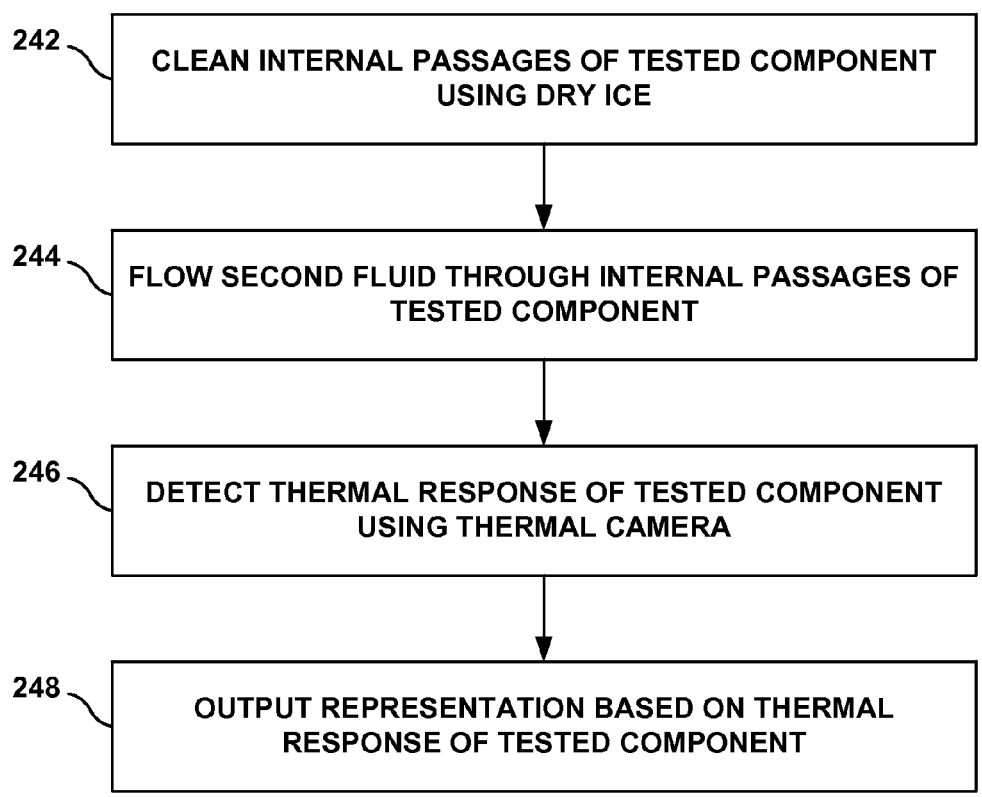
FIG. 11 is a flow diagram illustrating another example technique for cleaning a tested component using dry ice and performing flowing thermography on the tested component using a fluid.

FIG. 11 is a flow diagram illustrating an example technique that may be implemented by system 210 (e.g., under control of computing device 226) to clean tested component 212 using dry ice and perform flowing thermography on tested component 212 using a fluid. Although the technique of FIG. 11 will be described with respect to system 210 of FIG. 10, in other examples, the technique of FIG. 11 may be performed using a different system. Additionally, system 210 may perform other techniques to clean tested component 212 and perform flowing thermography on tested component 212.

The technique illustrated in FIG. 11 includes cleaning internal passages 228 of tested component 212 by introducing dry ice into internal passages 228 of tested component 212 (242). Computing device 226 may be configured to control dry ice source 222 to control introduction of dry ice into plenum 220, and, ultimately, internal passages 228 of tested component 212.

The dry ice may be in solid form, such as powder, pellets, shavings, or the like, and may impact any debris within internal passages 188. In some examples, contact with the dry ice may release at least some of the debris from the walls of internal passages 228 and the dry ice may remove the debris out of internal passages 228 through respective ones of exit orifices 230. In this way, the dry ice may be used to clean internal passages 228 of debris.

The technique of FIG. 11 also includes flowing the fluid through internal passages 228 of tested component 212 (244). To flow gaseous dry ice through internal passages 228, computing device 226 may be configured to control valve 236 to open a predetermined amount for a predetermined duration to cause a predetermined amount of the fluid to be released from fluid source 222 during the predetermined duration (e.g., a pulse of fluid). The pulse of fluid may flow through fluid line 238 to plenum 220, then through internal passages 228 and out exit orifices 230 defined in tested component 212.

The pulse of fluid may produce a transient temperature change in tested component 212 from an equilibrium temperature (e.g., the temperature of the surrounding atmosphere). In some examples, the fluid may be at a temperature lower, substantially the same as, or higher than the equilibrium temperature of tested component 212. The technique of FIG. 11 also includes detecting the thermal response of tested component 212 using thermal camera 218 (246). As the pulse of fluid flows through internal passages 228 and out through the corresponding exit orifices 230, thermal camera 218 may capture data representative of the temperature of the surface of tested component 212, with each individual sensor (e.g., corresponding to a pixel) of thermal camera 218 capturing data representative of the temperature of particular location of tested component 212 over time. The thermographic image data may include, for example, the wavelength and/or intensity of radiation detected by each individual sensor as a function of time. Computing device 226 may be configured to receive the thermographic image data from thermal camera 218.

The technique of FIG. 11 further includes outputting a representation based on the thermal response of tested component 212 (248). This step may be the similar or substantially the same as the outputting step of FIG. 9. For example, computing device 226 may process the thermographic image data received from thermal camera 218 to determine a single value representative of the thermal response of a location of tested component 212 (e.g., represented by a pixel or a set of adjacent pixels) over a duration of time.

In some examples, computing device 226 may be configured to combine thermographic image data from a plurality of thermography tests. In some examples, outputting a representation based on the thermal response of tested component 212 (248) may include outputting a false color or a grayscale representation of the thermographic image data. In some examples, computing device 226 may be configured to morph the thermographic image data to substantially align with three-dimensional master data as described above with respect to FIGS. 5-7, and computing device 226 may be configured to compare the thermographic image data to the three-dimensional master data to identify any potential deficiencies. In some examples, computing device 26 may be configured to receive the thermographic image data and flow rate data measured by at least one flow meter during, prior to, or after the flowing thermography test, as described above with respect to FIGS. 1-4.

In this way, in some examples, a system may be configured to both clean a tested component and perform flowing thermography on the component at a single testing station. Performing the cleaning and flowing thermography at a single inspection station may be more time and space efficient than utilizing two separate stations for the cleaning and the flowing thermography testing. Further, in examples in which gaseous dry ice is used to flowing thermography, cleaning and performing flowing thermography substantially simultaneously may be more time efficient that performing the procedures sequentially.

Although various examples have been described with reference to different figures, features of the examples and the examples themselves may be combined in various combinations. For example, the two-dimensional thermographic image data morphed to substantially align with the master image data may include quantitative flowing thermographic image data and/or may include data generated using flowing thermography with gaseous dry ice. As another example, the quantitative flowing thermographic image data may be determined using thermographic data generated using dry ice. Other combinations of the techniques described herein are also contemplated by this disclosure and will be apparent to those of ordinary skill in the art.

In one or more examples, the functions described herein may be implemented in hardware, software, firmware, or any combination thereof. If implemented in software, the functions may be stored on or transmitted over, as one or more instructions or code, a computer-readable medium or computer-readable storage device and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media or computer-readable storage device, which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used herein, include compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

Various examples have been described. These and other examples are within the scope of the following claims.

What is claimed is:

1. A system comprising:
   a source of dry ice;
   a thermal camera; and
   a computing device configured to:
      control the source of dry ice to cause dry ice to be introduced into an internal passage of a tested component to remove at least some debris from the internal passage;
      receive, from the thermal camera, thermographic image data representative of the thermal response of the tested component to the dry ice; and
      output a representation based on the thermographic image data.

2. The system of claim 1, wherein the thermographic image data comprises data representative of thermal response to the dry ice of each respective location of a plurality of locations of the tested component, and wherein the computing device is configured to determine a respective single value representative of the thermal response of the component for each respective location.

3. The system of claim 2, wherein the computing device is configured to output the representation based on the thermographic image data by at least outputting a representation based on the respective single values.

4. The system of claim 1, wherein the computing device is further configured to:
   receive master image data including three-dimensional image data representative of a geometry and a thermal response of at least one of a theoretical component, a fabricated gold standard component, or an average of a plurality of components;
   morph the thermographic image data to substantially align with the three-dimensional image data and produce morphed thermographic image data; and
   wherein the computing device is configured to output the representation based on the thermographic image data by at least outputting a representation based on the morphed thermographic image data for display.

5. The system of claim 1, further comprising at least one flow meter and a plenum, wherein the computing device is further configured to:

receive flow rate values from the at least one flow meter relating to flow testing of a first component fluidically coupled to plenum, wherein the first component and the tested component have substantially similar geometry; and associate the flow rate values with the thermographic image data to produce quantitative flowing thermographic image data.

6. A method comprising:

controlling, by a computing device, a source of dry ice to cause dry ice to be introduced into an internal passage of a tested component to remove at least some debris from the internal passage;

receiving, by the computing device, from a thermal camera, thermographic image data representative of the thermal response of the tested component to the dry ice; and outputting, by the computing device, a representation based on the thermographic image data.

7. The method of claim 6, wherein the thermographic image data comprises data representative of thermal response to the dry ice of each respective location of a plurality of locations of the tested component, and further comprising determining, by the computing device, a respective single value representative of the thermal response of the component for each respective location.

8. The method of claim 7, wherein outputting the representation based on the thermographic image data comprises outputting a representation based on the respective single values.

9. The method of claim 6, further comprising:

receiving, by the computing device, master image data including three-dimensional image data representative of a geometry and a thermal response of at least one of a theoretical component, a fabricated gold standard component, or an average of a plurality of components;

morphing, by the computing device, the thermographic image data to substantially align with the three-dimensional image data and produce morphed thermographic image data; and wherein outputting the representation based on the thermographic image data comprises outputting a representation based on the morphed thermographic image data for display.

10. The method of claim 6, further comprising:

receiving, by the computing device, flow rate values from at least one flow meter relating to flow testing of a first component fluidically coupled to a plenum, wherein the first component and the tested component have substantially similar geometry; and associating, by the computing device, the flow rate values with the thermographic image data to produce quantitative flowing thermographic image data.

11. A non-transitory computer readable storage medium comprising instructions that, when executed, cause at least one processor to:

control a source of dry ice to cause dry ice to be introduced into an internal passage of a tested component to remove at least some debris from the internal passage;

receive, from a thermal camera, thermographic image data representative of the thermal response of the tested component to the dry ice; and output a representation based on the thermographic image data.

12. The non-transitory computer readable storage medium of claim 11, wherein the thermographic image data comprises data representative of thermal response to the dry ice of each respective location of a plurality of locations of the tested component, and further comprising instructions that, when executed, cause the at least one processor to determine a respective single value representative of the thermal response of the component for each respective location.

13. The non-transitory computer readable storage medium of claim 11, further comprising instructions that, when executed, cause the at least one processor to:

receive master image data including three-dimensional image data representative of a geometry and a thermal response of at least one of a theoretical component, a fabricated gold standard component, or an average of a plurality of components;

morph the thermographic image data to substantially align with the three-dimensional image data and produce morphed thermographic image data; and wherein the instructions that, when executed, cause the at least one processor to output the representation based on the thermographic image data comprise instructions that, when executed, cause the at least one processor to output a representation based on the morphed thermographic image data for display.

14. The non-transitory computer readable storage medium of claim 11, further comprising instructions that, when executed, cause the at least one processor to:

receive flow rate values from at least one flow meter relating to flow testing of a first component fluidically coupled to a plenum, wherein the first component and the tested component have substantially similar geometry; and associate the flow rate values with the thermographic image data to produce quantitative flowing thermographic image data.

* * * * *